(12) United States Patent
Gil et al.

(10) Patent No.: US 11,324,703 B2
(45) Date of Patent: May 10, 2022

(54) SURFACTANT PEPTIDE NANOSTRUCTURES AND USES THEREOF IN DRUG DELIVERY

(71) Applicant: 3-D Matrix, Ltd., Tokyo (JP)

(72) Inventors: Eun Seok Gil, Acton, MA (US); Elton Aleksi, West Roxbury, MA (US); Noriaki Matsuda, Tokyo (JP)

(73) Assignee: 3-D Matrix, Ltd., Tokyo (JP)

( * ) Notice: Subject to any disclaimer, the term of this patent is extended or adjusted under 35 U.S.C. 154(b) by 0 days.

(21) Appl. No.: 16/206,319

(22) Filed: Nov. 30, 2018

(65) Prior Publication Data

US 2019/0231706 A1 Aug. 1, 2019

Related U.S. Application Data

(60) Provisional application No. 62/599,566, filed on Dec. 15, 2017.

(51) Int. Cl.
| | |
|---|---|
| *A61K 9/00* | (2006.01) |
| *A61K 9/51* | (2006.01) |
| *A61K 47/42* | (2017.01) |
| *A61K 31/713* | (2006.01) |
| *A61K 9/08* | (2006.01) |
| *A61K 31/7105* | (2006.01) |
| *A61K 45/06* | (2006.01) |

(52) U.S. Cl.
CPC .......... *A61K 9/5169* (2013.01); *A61K 9/0019* (2013.01); *A61K 9/0092* (2013.01); *A61K 9/08* (2013.01); *A61K 9/5192* (2013.01); *A61K 31/713* (2013.01); *A61K 47/42* (2013.01); *A61K 31/7105* (2013.01); *A61K 45/06* (2013.01)

(58) Field of Classification Search
None
See application file for complete search history.

(56) References Cited

U.S. PATENT DOCUMENTS

| | | |
|---|---|---|
| 4,466,641 A | 8/1984 | Heilman et al. |
| 4,582,640 A | 4/1986 | Smestad et al. |
| 4,642,117 A | 2/1987 | Nguyen et al. |
| 4,947,840 A | 8/1990 | Yannas et al. |
| 5,110,604 A | 5/1992 | Chu et al. |
| 5,126,141 A | 6/1992 | Henry |
| 5,236,903 A | 8/1993 | Saiki et al. |
| 5,292,514 A | 3/1994 | Capecchi et al. |
| 5,510,102 A | 4/1996 | Rum |
| 5,527,610 A | 6/1996 | Urry |
| 5,550,187 A | 8/1996 | Rhee et al. |
| 5,670,483 A | 9/1997 | Zhang et al. |
| 5,736,392 A | 4/1998 | Hawley-Nelson et al. |
| 5,747,452 A | 5/1998 | Ruoslahti et al. |
| 5,773,577 A | 6/1998 | Cappello |
| 5,955,343 A | 9/1999 | Holmes et al. |
| 6,046,160 A | 4/2000 | Obi-Tabot |
| 6,224,893 B1 | 5/2001 | Langer et al. |
| 6,280,474 B1 | 8/2001 | Cassidy et al. |
| 6,428,811 B1 | 8/2002 | West et al. |
| 6,548,630 B1 | 4/2003 | Zhang et al. |
| 6,730,298 B2 | 5/2004 | Griffith-Cima et al. |
| 6,800,481 B1 | 10/2004 | Holmes et al. |
| 7,179,784 B2 | 2/2007 | Zhang et al. |
| 7,671,258 B2 | 3/2010 | Zhang et al. |
| 8,748,111 B2 | 6/2014 | Mershin et al. |
| 9,084,837 B2 | 7/2015 | Ellis-Behnke et al. |
| 9,133,484 B2 | 9/2015 | Yoshida et al. |
| 9,140,677 B2 | 9/2015 | Mershin et al. |
| 9,162,005 B2 | 10/2015 | Ellis-Behnke et al. |
| 9,327,010 B2 | 5/2016 | Ellis-Behnke et al. |
| 9,339,476 B2 | 5/2016 | Norchi et al. |
| 9,364,513 B2 | 6/2016 | Ellis-Behnke et al. |
| 9,415,084 B2 | 8/2016 | Ellis-Behnke et al. |
| 9,439,941 B2 | 9/2016 | Ellis-Behnke et al. |
| 10,245,299 B2 | 4/2019 | Mehta et al. |
| 10,337,012 B2 | 7/2019 | Ochiya |
| 2002/0160471 A1 | 10/2002 | Kisiday et al. |
| 2003/0069177 A1 | 4/2003 | Dubaquie et al. |
| 2003/0166846 A1 | 9/2003 | Rothstein et al. |
| 2003/0176335 A1 | 9/2003 | Zhang et al. |
| 2004/0204561 A1 | 10/2004 | Ellison |
| 2005/0181973 A1 | 8/2005 | Genove et al. |
| 2006/0084607 A1 | 4/2006 | Spirio et al. |
| 2006/0148703 A1 | 7/2006 | Lee et al. |

(Continued)

FOREIGN PATENT DOCUMENTS

| | | |
|---|---|---|
| CA | 2572964 A1 | 2/2006 |
| CN | 101514225 A | 8/2009 |

(Continued)

OTHER PUBLICATIONS

Henin et al., "Conformational Equilibrium in Alanine-Rich Peptides Probed by Reversible Stretching Simulations," J. Phys. Chem. B 110:16718-16723 (2006) (Year: 2006).*
Zhu et al., "Functional vesicles formed by anticancer drug assembly," Bioorganic & Medicinal Chemistry Letters 25:188-191 (2015) (Year: 2015).*
Wang et al., "Morphology-controlled synthesis of silica materials templated by self-assembled short amphiphilic peptides," RSC advances 3:15955-15965 (2013) (Year: 2013).*
Biosynthesis, "N-Terminal Acetylation Amidation Peptides Chemically Synthesized Aminopeptidases Intracellular," 1 page, (2008), accessed Apr. 25, 2018 (Year: 2008).*
Han et al., "Self-Assembly of Short Peptide Amphiphiles: The Cooperative Effect of Hydrophobic Interaction and Hydrogen Bonding, " Chem. Eur. J.17: 13095-13102 (2011) (Year: 2011).*

(Continued)

*Primary Examiner* — Julie Ha
*Assistant Examiner* — Kristina M Hellman
(74) *Attorney, Agent, or Firm* — IP Supra, PLLC; Constantine Linnik; Beth L. Smiley

(57) ABSTRACT

Disclosed herein are surfactant peptide nanostructures wherein the peptides have repeating hydrophobic amino acids in an integer equal to or less than four. The peptide nanostructures are useful for therapeutic applications, including for delivery of drugs and siRNA.

13 Claims, 18 Drawing Sheets

Specification includes a Sequence Listing.

(56) References Cited

U.S. PATENT DOCUMENTS

| | | |
|---|---|---|
| 2006/0211615 A1 | 9/2006 | Zhang et al. |
| 2007/0157967 A1 | 7/2007 | Mershin et al. |
| 2008/0032934 A1 | 2/2008 | Ellis-Behnke et al. |
| 2008/0091233 A1 | 4/2008 | Ellis-Behnke et al. |
| 2009/0069547 A1 | 3/2009 | Zhang |
| 2009/0162437 A1 | 6/2009 | Horii et al. |
| 2009/0169598 A1 | 7/2009 | Crutcher |
| 2010/0143504 A1 | 6/2010 | Spirio et al. |
| 2011/0152203 A1 | 6/2011 | Yoshida et al. |
| 2011/0201541 A1 | 8/2011 | Takamura et al. |
| 2012/0021932 A1 | 1/2012 | Mershin et al. |
| 2013/0236891 A1 | 9/2013 | Ochiya |
| 2013/0281547 A1 | 10/2013 | Spirio et al. |
| 2014/0038909 A1 | 2/2014 | Takamura et al. |
| 2014/0099729 A1 | 4/2014 | Mershin et al. |
| 2014/0364330 A1 | 12/2014 | Mershin et al. |
| 2015/0147384 A1 | 5/2015 | Koutsopoulos et al. |
| 2015/0197359 A1 | 7/2015 | Nohara et al. |
| 2015/0328279 A1 | 11/2015 | Ellis-Behnke et al. |
| 2016/0015855 A1 | 1/2016 | Nohara et al. |
| 2016/0317607 A1 | 11/2016 | Spirio et al. |
| 2016/0362451 A1 | 12/2016 | Gil et al. |
| 2017/0072008 A1 | 3/2017 | Mehta et al. |
| 2017/0173105 A1 | 6/2017 | Mehta et al. |
| 2017/0173221 A1 | 6/2017 | Mehta et al. |
| 2017/0202986 A1 | 7/2017 | Gil et al. |
| 2017/0240902 A1 | 8/2017 | Ochiya |
| 2018/0369452 A1 | 12/2018 | Maki et al. |

FOREIGN PATENT DOCUMENTS

| | | |
|---|---|---|
| EP | 3031466 A1 | 6/2016 |
| EP | 3545961 A1 | 10/2019 |
| JP | 2005-515796 A | 6/2005 |
| JP | 2007-105186 A | 4/2007 |
| JP | 2007-526232 A | 9/2007 |
| JP | 2008-505919 A | 2/2008 |
| JP | 5255274 B2 | 8/2013 |
| JP | 5730828 B2 | 6/2015 |
| JP | 5922749 B2 | 5/2016 |
| JP | 2017-082002 A | 5/2017 |
| WO | WO-94/17811 A1 | 8/1994 |
| WO | WO-96/040961 A1 | 12/1996 |
| WO | WO-1996/040033 A1 | 12/1996 |
| WO | WO-1997/037694 A1 | 10/1997 |
| WO | WO-2002/058749 A2 | 8/2002 |
| WO | WO-2002/062961 A2 | 8/2002 |
| WO | WO-2003/006043 A1 | 1/2003 |
| WO | WO-03/084980 A2 | 10/2003 |
| WO | WO-03/096972 A2 | 11/2003 |
| WO | WO-2004/007532 A2 | 1/2004 |
| WO | WO-2005/014615 A2 | 2/2005 |
| WO | WO-2006/014570 A2 | 2/2006 |
| WO | WO-2006/116524 A1 | 11/2006 |
| WO | WO-2007/070645 A2 | 6/2007 |
| WO | WO-2007/142757 A2 | 12/2007 |
| WO | WO-2008/039483 A2 | 4/2008 |
| WO | WO-2008/073392 A2 | 6/2008 |
| WO | WO-2008/073395 A2 | 6/2008 |
| WO | WO-2008/113030 A2 | 9/2008 |
| WO | WO-2008/134544 A1 | 11/2008 |
| WO | WO-2008/136820 A1 | 11/2008 |
| WO | WO-2009/018467 A2 | 2/2009 |
| WO | WO-2010/014903 A1 | 2/2010 |
| WO | WO-2010/024262 A1 | 3/2010 |
| WO | WO-2010/041636 A1 | 4/2010 |
| WO | WO-2012/023345 A1 | 2/2012 |
| WO | WO-2013/181511 A1 | 12/2013 |
| WO | WO-2014/008400 A2 | 1/2014 |
| WO | WO-2014/136081 A1 | 9/2014 |
| WO | WO-2015/027203 A1 | 2/2015 |
| WO | WO-2015/136370 A2 | 9/2015 |
| WO | WO-2015/138473 A1 | 9/2015 |
| WO | WO-2015/138475 A1 | 9/2015 |
| WO | WO-2015/138478 A1 | 9/2015 |
| WO | WO-2015/138514 A1 | 9/2015 |
| WO | WO-2017/120092 A1 | 7/2017 |
| WO | WO-2017/164334 A1 | 9/2017 |
| WO | WO-2018/097335 A1 | 5/2018 |
| WO | WO-2019/093308 A1 | 5/2019 |
| WO | WO-2019/116092 A1 | 6/2019 |

OTHER PUBLICATIONS

Martinez-Rodriguez et al., "natural occurrence and industrial applications of D-amino acids: an overview", Chemistry and biodiversity 7: 1531-1548 (2010) (Year: 2010).*

Aggeli, A. et al., Hierarchical self-assembly of chiral rod-like molecules as a model for peptide β-sheet tapes, ribbons, fibrils, and fibers, *Nature*, 386: 259-262 (1997).

Langer, R.S. and Vacanti, J.P., Tissue Engineering, *Science*, 260: 920-926 (1993).

Le Maire, M. et al., Interaction of membrane proteins and lipids with solubilizing detergents, *Biochim. Biophys. Acta.*, 7508(1-2):1508:86-111 (2000).

Liu, Y. et al., Genomic analysis of membrane protein families: abundance and conserved motifs, Genome Biology, 3(10):research0054. 1-0054.12 (2002).

Okada, T, et al., Functional role of internal water molecules in rhodopsin revealed by X-ray crystallography, *Proc. Natl. Acad. Sci. USA*, 99:5982-5987 (2002).

Vauthey, S et al., Molecular self-assembly of surfactant-like peptides to form nanotubes and nanovesicles, *Proc. Natl. Acad. Sci. USA*, 99(8):5355-5360 (2002).

Wallin, E. and Von Heijne, G., Genome-wide analysis of integral membrane proteins from eubacterial, archaean, and eukaryotic organisms, *Protein Sci.*, 7:1029-1038 (1998).

Whitesides, G.M. et al., Molecular self-assembly and nanochemistry: a chemical strategy for the synthesis of nanostructures, *Science*, 254:1312-1319 (1991).

Zhang, S. and Rich, A., Direct conversion of an oligopeptide from a β-sheet to an α-helix: A model for amyloid formation, *Proc. Natl. Acad. Sci. USA*, 94(1): 23-28 (1997).

Zhang, S. et al., Biological Surface Engineering: A Simple System for Cell Pattern Formation, *Biomaterials*, 20:1213-1220 (1999).

Zhang, S., Spontaneous assembly of a self-complementary oligopeptide to form a stable macroscopic membrane, *Proc. Natl. Acad. Sci. USA*, 90: 3334-3338 (1993).

Cenker, C. C. et al., Aqueous Self-Assembly within the Homologous Peptide Series $A_nK$, Langmuir, 30: 10072-10079 (2014).

Chen, C. et al., Antibacterial Activities of Short Designer Peptides: a Link between Propensity for Nanostructuring and Capacity for Membrane Destabilization, Biomacromolecules, 11(2): 402-411 (2010).

Database WPI, Week 201737, Thomson Scientific, London, GB, AN 2017-32140K.

International Search Report for PCT/IB2018/001511 (Surfactant Peptide Nanostructures and Uses in Drug Delivery, filed Nov. 30, 2018), issued by ISA/EPO, 6 pages (Mar. 29, 2019).

Written Opinion for PCT/IB2018/001511 (Surfactant Peptide Nanostructures and Uses in Drug Delivery, filed Nov. 30, 2018), issued by ISA/EPO, 10 pages (Mar. 29, 2019).

Yoshida, D. et al., A transfection method for short interfering RNA with the lipid-like self-assembling nanotube, A6K, Medical Molecular Morphology, 46(2): 86-91 (2013).

3-D Matrix Japan, Ltd. Company Profile Power Point, 32 pages, May 2005 (with English translation).

3-D Matrix Japan, Ltd., Products and FAQs, with English Translation, 14 pages. URL: http:/web.archive.org [Retrieved Oct. 21, 2016].

3D Matrix Japan, Company, Technology, Products, Technology, FAQs, Publication, Company, News, Contact, no English translation, 17 pages. URL: http://www.3d-matrix.co.jp/cm02.html [Retrieved Feb. 25, 2005].

3D Matrix Japan, Product Features, with English translation, 2 pages. URL: http://web.archive.org/web/20050416044014/http://www.3d-matrix.eo.jp/pr03.html [Retrieved Feb. 20, 2013].

(56) References Cited

OTHER PUBLICATIONS

3D Matrix Japan, Product List, with English translation, 2 pages. URL: http://web.archive.org/web/20050416043834/http://www.3d-matrix.co.jp/pr02.html [Retrieved Aug. 1, 2013].
3D Matrix Japan, Products, with English translation, 2 pages. URL: http://web.archive.org/web/20050415004502/http://www.3d-matrix.co.jp/pr0I.html [Retreived Feb. 20, 2013].
3D-Matrix Japan, Products, FAQs, 8 pages, dispatched Sep. 20, 2011 [English translation].
Abukawa, H. et al., Reconstructing Mandibular Defects Using Autologous Tissue-Engineered Tooth and Bone Constructs, J. Oral Maxillofac. Surg., 67(2):335-347 (2009).
Allen, P. et al., Type I collagen, fibrin and PuraMatrix matrices provide permissive environments for human endothelial and mesenchymal progenitor cells to form neovascular networks, J. Tissue Eng. Regen Med., 5(4):e74-86 (2011).
Altman, M. et al., Conformational behavior of ionic self-complementary peptides, Protein Sci., 9(6):1095-105 (2000).
Anderson, I. The properties of hyaluronan and its role in wound healing, Prof. Nurse., 17(4):232-5 (2001).
Author Not Known, Medical Devices: Guidance Document, Borderline products, drug-delivery products and medical devices incorporating, as an integral part, an ancillary medicinal substance or an ancillary human blood derivative, European Commission, DG Enterprise and Industry, Directorate F, Unit F3 "Cosmetics and medical devices", 22 pages (Dec. 3, 2009) <http://ec.europa.eu/health/medical-devices/files/meddev/2_1_3_rev_3-12_2009_en.pdf> [last accessed on May 4, 2015].
Author Unknown, ISO 13485, Wikipedia, retrieved from <<https://en.wikipedia.org/w/index.php?title=IS0 13485&oldid=694123721>>. Accessed on Dec. 2, 2016.
Author Unknown, Medical Device, Wikipedia, retrieved from <<https://en.wikipedia.org/w/index.php?title=Medical_device&oldid=699710004>>, retrieved on Dec. 2, 2016.
BD PuraMatrix Peptide Hydrogel, Catalog No. 354250, BD Biosciences, 1-16 (2004).
BD PuraMatrix Peptide Hydrogel, Product Specification Sheet, 1 page.
Beam, J., Wound Cleansing: Water or Saline?, Journal of Athletic Training, 41(2): 196-197 (2006).
Bouten, C.V et al., Substrates for cardiovascular tissue engineering, Adv. Drug Deliv. Rev., 63(4-5):221-41 (2011).
Branco, M.C. and Schneider, J.P., Self-assembling materials for therapeutic delivery, Acta. Biomaterialia, 5(3): 817-831 (2009).
Caplan, M.R. et al., Control of self-assembling oligopeptide matrix formation through systematic variation of amino acid sequence, Biomaterials, 23(1):219-27 (2002).
Caplan, M.R. et al., Effects of systematic variation of amino acid sequence on the mechanical properties of a self-assembling, oligopeptide biomaterial, J. Biomater. Sci. Polymer Edn., 13(3):225-236 (2002).
Caplan, M.R. et al., Self-assembly of a beta-sheet protein governed by relief of electrostatic repulsion relative to van der Waals attraction, Biomacromolecules, 1(4):627-31 (2000).
Censi, R. et al., Hydrogels for protein delivery in tissue engineering, J. Control Release, 161(2):680-692 (2012).
Chen, K. et al., A Hybrid Silk/RADA-Based Fibrous Scaffold with Triple Hierarchy for Ligament Regeneration, Tissue Eng. Part A., 18(13-14):1399-409 (2012).
Chen, P., Self-assembly of ionic-complementary peptides: a physicochemical viewpoint, Colloids and Surfaces A: Physicochemical and Engineering Aspects, 261(1-3): 3-24 (2005).
Cigognini, D. et al., Evaluation of early and late effects into the acute spinal cord injury of an injectable functionalized self-assembling scaffold, PLoS One., 6(5): e19782 (2011).
Concaro, S. et al., Effect of different materials on the proliferation and migration of articular chondrocytes, Osteoarthritis and Cartilage, 15:Supplement B, pp. B119 (2007).
Cooper et al., "Testing the "critical-size" in calvarial bone defects: revisiting the concept of a critical-sized defect (CSD)," Plast Reconstr Surg. 125(6): 1685-1692, 2010.
Cunha, C. et al., Emerging nanotechnology approaches in tissue engineering for peripheral Nerve regeneration, Nanomedicine, 7(1):50-59 (2011).
Curley, J.L. et al., Fabrication of micropatterned hydrogels for neural culture systems using dynamic mask projection photolithography, J. Vis. Exp., 48: 2636 (2011).
Davis, M.E. et al., Custom design of the cardiac microenvironment with biomaterials, Circ Res., 97(1):8-15(2005).
Davis, M.E. et al., Local myocardial insulin-like growth factor 1 (IGF-1) delivery with biotinylated peptide nanofibers improves cell therapy for myocardial infarction, Proc. Natl. Acad. Sci. USA. ,103(21):8155-8160 (2006).
Davis, M.E. et al., Injectable self-assembling peptide nanofibers create intramyocardial microenvironments for endothelial cells, Circulation, 111 (4):442-50 (2005).
Declaration of Dr. Terence Norchi, MD, for use in proceedings against EP 1879606, 4 pages (Mar. 31, 2016).
Declaration of Rutledge Ellis-Behnke for WO 2006/116524, 6 pages, Aug. 10, 2015.
Declaration of Shuguang Zhang for U.S. Appl. No. 13/122,758, 12 pages, executed Feb. 9, 2016.
Declaration of Steven A. Kates, Third Party of Observations to EPO on EP Application No. 05770153.4, Aug. 13, 2014.
Declaration of Thomas Francis O'Donnell Jr., Third Party Observations to EPO on EP Application No. 05770153.4, Aug. 12, 2014.
Dutta, R.C. and Dutta, A.K., Comprehension of ECM-Cell dynamics: A prerequisite for tissue regeneration, Biotechnol. Adv., 28(6):764-769 (2010).
Dégano, I.R. et al., The effect of self-assembling peptide nanofiber scaffolds on mouse embryonic fibroblast implantation and proliferation, Biomaterials, 30(6):1156-65 (2009).
Eisenbud, D. et al., Hydrogel Wound Dressings: Where Do We Stand in 2003?, Ostomy Wound Manage, 49(10): 52-57 (2003).
Ellis-Behnke, R. et al., Crystal clear surgery with self-assembling molecules that act as a barrier in the brain and intestine, Abstracts 1 Nanomedicine: Nanotechnology, Biology, and Medicine, 1:269-270 (2005).
Ellis-Behnke, R., At the nanoscale: nanohemostat, a new class of hemostatic agent, WIREs Nanomedicine and Nanobiotechnology, 3: 70-78 (2011).
Ellis-Behnke, R.G. et al., Nano neuro knitting: peptide nanofiber scaffold for brain repair and axon regeneration with functional return of vision, Proc. Natl. Acad. Sci. USA, 103(13):5054-5059 (2006).
Ellis-Behnke, R.G. et al., Nano hemostat solution: immediate hemostasis at the nanoscale, Nanomedicine, 2(4):207-15 (2006).
Experimental Report conducted at Arch Therapeutics, $(EAKA)_4$ Acetate, 6 pages, (Jul. 2014).
Experimental Report conducted by Ellis-Behnke, 1. Kidneys (rats), received May 12, 2017.
Garreta, E. et al., Osteogenic differentiation of mouse embryonic stem cells and mouse embryonic fibroblasts in a three-dimensional self-assembling peptide scaffold, Tissue Eng., 12(8):2215-27 (2006).
Gelain, F. et al., Designer self-assembling peptide scaffolds for 3-d tissue cell cultures and regenerative medicine, Macromol. Biosci., 7(5):544-51 (2007).
Gelain, F. et al., Slow and sustained release of active cytokines from self-assembling peptide scaffolds, Journal of Controlled Release, 145:231-239 (2010).
Gervaso, F. et al., The biomaterialist's task: scaffold biomaterials and fabrication technologies, Joints 1(3): 130-137 (2013).
Gherli, T. et al., Comparing warfarin with aspirin after biological aortic valve replacement: a prospective study, Circulation, 110(5):496-500 (2004).
Giri, S. and Bader, A., Improved preclinical safety assessment using micro-BAL devices: the potential impact on human discovery and drug attrition, Drug Discov. Today, 16(9-10):382-397 (2011).
Gonzales, A.L. et al., Integrin interactions with immobilized peptides in polyethylene glycol diacrylate hydrogels, Tissue Eng., 10(11-12):1775-86 (2004).

(56) References Cited

OTHER PUBLICATIONS

Guo, H.D. et al., Sustained delivery of VEGF from designer self-assembling peptides improves cardiac function after myocardial infarction, Biochem. Biophys. Res. Commun., 424(1):105-111 (2012).
Guo, H.D. et al., Transplantation of marrow-derived cardiac stem cells carried in designer self-assembling peptide nanofibers improves cardiac function after myocardial infarction, Biochem. Biophys. Res. Commun., 399(1):42-48 (2010).
Guo, J. et al., Reknitting the injured spinal cord by self-assembling peptide nanofiber scaffold, Nanomedicine, 3(4):311-321 (2007).
Gurski, L.A. et al., 3D Matrices for Anti-Cancer Drug Testing and Development, Oncology, Issues Jan./Feb. 2010: 20-25.
Hartgerink, J.D. et al., Peptide-amphiphile nanofibers: a versatile scaffold for the preparation of self-assembling materials, Proc. Natl. Acad. Sci. U S A., 99(8):5133-8 (2002).
Hemmrich, K. et al., Implantation of preadipocyte-loaded hyaluronic acid-based scaffolds into nude mice to evaluate potential for soft tissue engineering, Biomaterials, 26(34):7025-37 (2005).
Henriksson, H. et al., Investigation of different cell types and gel carriers for cell-based intervertebral disc therapy, in vitro and in vivo studies, J. Tissue Eng. Regen. Med., doi: 10.1002/term.480 (2011).
Henriksson, H.B. et al., Transplantation of human mesenchymal stems cells into intervertebral discs in a senogeneic porcine model, Spine (Phila Pa 1976), 34(2):141-148 (2009).
Hilton, J. R. et al., Wound Dressings in Diabetic Foot Disease, Clinical Infectious Diseases, 39: S100-3 (2004).
Hollinger, J.O. and Kleinschmidt, J.C., "The critical size defect as an experimental model to test bone repair materials," J. Craniofac Surg 1990(1): 60-68.
Holmes, T.C. et al., Extensive neurite outgrowth and active synapse formation on self-assembling peptide scaffolds, Proc. Natl. Acad. Sci. U S A., 97(12):6728-33 (2000).
Horii, A. et al., Biological designer self-assembling peptide nanofiber scaffolds significantly enhance osteoblast proliferation, differentiation and 3-D migration, PLoS One, 2(2):e190 (2007).
Hsieh, P.C. et al., Controlled delivery of PDGF-BB for myocardial protection using injectable self-assembling peptide nanofibers, J. Clin. Invest., 116(1):237-248 (2006).
Hsieh, P.C.H. et al., Local controlled intramyocardial delivery of platelet-derived growth factor improves postinfarction ventricular function without pulmonary toxicity, Circulation, 114(7):637-644 (2006).
Huang, A.H. et al., Mechanics and mechanobiology of mesenchymal stem cell-based engineered cartilage, J. Biomech., 43(1):128-136 (2010).
Hwang, W. et al., Supramolecular structure of helical ribbons self-assembled from a betasheet peptide, The Journal of Chemical Physics, 118(1): 389-397 (2003).
Kates, Declaration of Steven Kates, Ph.D., RE: Japanese Patent Application No. 2008-509090 ("Third Party Declaration") (2012).
Kim, J.H. et al., The enhancement of mature vessel formation and cardiac function in infarcted hearts using dual growth factor delivery with self-assembling peptides, Biomaterials, 32(26):6080-6088 (2011).
Kisiday, J. et al., Self-assembling peptide hydrogel fosters chondrocyte extracellular matrix production and cell division: implications for cartilage tissue repair, Proc. Natl. Acad. Sci. U S A, 99(15):9996-10001 (2002).
Kohgo, T. et al, Poster 110: Bone Regeneration for Dental Implants Using Tissue-Engineered Bone With Self-Assembling Peptide Nanofiber 3-Dimensional (3D) Scaffolds, Journal of Oral and Maxillofacial Surgery, 65(9): Supplement, p. 43.e63 (2007).
Komatsu, S. et al, The Neutral Self-Assembling Peptide Hydrogel SPG-178 as a Topical Hemostatic Agent, PLoS ONE, 9(7): e102778 (2014).
Kopecek, J. and Yang, J., Peptide-directed self-assembly of hydrogels, Acta Biomaterialia, 5(3): 805-816 (2009).

Kumada, Y. and Zhang, S., Significant type I and type III collagen production from human periodontal ligament fibroblasts in 3D peptide scaffolds without extra growth factors, PLoS One, 5(4):e10305 (2010).
Kumada, Y. et al., Functionalized scaffolds of shorter self-assembling peptides containing MMP-2 cleavable motif promote fibroblast proliferation and significantly accelerate 3-D cell migration independent of scaffold stiffness, Soft Matter, The Royal Society of Chemistry, 7 pages (2010).
Kyle, S. et al., Production of self-assembling biomaterials fortissue engineering, Trends Biotechnol., 27(7):423-33 (2009).
Lampe, K.J. and Heilshorn, S.C., Building stem cell niches from the molecule up through engineered peptide materials, Neurosci. Lett., 519(2):138-46 (2012).
Lee, J. et al., Three-dimensional cell culture matrices: state ofthe art, Tissue Eng. Part B Rev., 14(1):61-86 (2008).
Leon, E.J. et al., Mechanical properties of a self-assembling oligopeptide matrix, J. Biomater. Sci. Polymer Edn., 9(3):297-312 (1998).
Leung, G.K. et al, Peptide nanofiber scaffold for brain tissue reconstruction, Methods Enzymol., 508:177-190 (2012).
Li, X. et al, Engineering neural stem cell fates with hydrogel design for central nervous system regeneration, Progress in Polymer Science, 37(8):1105-1129 (2012).
Liedmann, A. et al., Cultivation of human neural progenitor cells in a 3-dimensional selfassembling peptide hydrogel, J. Vis. Exp., (59):e3830 (2012).
Liu, J. et al., Controlled release of paclitaxel from a self-assembling peptide hydrogel formed in situ and antitumor study in vitro, International Journal of Nanomedicine, 6:2143-2153 (2011).
Liu, W-M. et al., Diversification of Microfluidic Chip for Applications in Cell-Based Bioanalysis, Chinese Journal of Analytical Chemistry, 40(1): 24-31 (2012).
Loo, Y. et al., From short peptides to nanofibers to macromolecular assemblies in biomedicine, Biotechnol. Adv., 30(3):593-603 (2012).
Luo, Z. and Zhang, S., Designer nanomaterials using chiral self-assembling peptide systems and their emerging benefit for society, Chem. Soc. Rev., 41(13):4736-54 (2012).
Luo, Z. et al, Fabrication of self-assembling d-form peptide nanofiber scaffold d-EAK16 for rapid hemostasis, Biomaterials, 32(8):2013-20 (2011).
Maher, S.A. et al, A nano-fibrous cell-seeded hydrogel promotes integration in a cartilage gap model, J. Tissue Eng. Regen. Med., 4(1):25-29 (2010).
Marini, D.M. et al., Left-Handed Helical Ribbon Intermediates in the Self-Assembly of a beta-Sheet Peptide, Nano Letters, 2(4):295-299 (2002).
Marston, W.A. et al., Initial report of the use of an injectable porcine collagen-derived matrix to stimulate healing of diabetic foot wounds in humans, Wound Repair Regen., 13(3):243-7 (2005).
Masuhara, H. et al, Novel infectious agent-free hemostatic material (TDM-621) in cardiovascular surgery, Ann. Thorac. Cardiovasc. Surg. Methods Enzymol., 18(5):444-451 (2012).
McGrath, A.M. et al, BD© PuraMatrix® peptide hydrogel seeded with Schwann cells for peripheral nerve regeneration, Brain Res. Bull., 83(5):207-213 (2010).
Meng, H. et al, Peripferal Nerve Regeneration in Response to Synthesized Nanofiber Scaffold Hydrogel, Life Science Journal, 9(1): 42-46 (2012).
Misawa, H. et al, PuraMatrix facilitates bone regeneration in bone defects of calvaria in mice, Cell Transplant, 15(10):903-910 (2006).
Mooney, M.P. and Siegel, M.I., Animal models for bone tissue engineering of critical-sized defects (CSDs), bone pathologies, and orthopedic disease states, In: Hollinger, JO.; Einhorn, TA.; Doll, BA.; Sfeir, C.,editors. Bone Tissue Engineering. Boca Raton, FL: C.R.C. Press, pp. 217-244 (2005).
Nakahara, H. et al, Bone repair using a hybrid scaffold of self-assembling peptide PuraMatrix and polyetheretherketone cage in rats, Cell Transplant, 19(6):791-797 (2010).
Narmoneva, D.A. et al, Endothelial cells promote cardiac myocyte survival and spatial reorganization: implications for cardiac regeneration, Circulation, 110(8):962-968 (2004).
Narmoneva, D.A. et al., Self-assembling short oligopeptides and the promotion of angiogenesis, Biomaterials, 26(23):4837-46 (2005).

(56) References Cited

OTHER PUBLICATIONS

Nichol, J.W. et al, Co-culture induces alignment in engineered cardiac constructs via MMP-2 expression, Biochem. Biophys. Res. Commun., 373(3):360-365 (2008).
Nishimura, A. et al., Controlled release of insulin from self-assembling nanofiber hydrogel, PuraMatrix: application for the subcutaneous injection in rats, European Journal of Pharmaceutical Sciences, 45:1-7 (2012).
Ortinau, S. et al, Effect of 3D-scaffold formation on differentiation and survival in human neural progenitor cells, Biomed. Eng. Online, 9(1):70 (2010).
Osterman, D.G. and Kaiser, E.T., Design and characterization of peptides with amphiphilic beta-strand structures, J. Cell Biochem., 29(2):57-72 (1985).
Patterson, J. et al., Biomimetic materials in tissue engineering, Materialstoday, 13(1-2): 14-22 (2010).
Saiga, K. et al, Combined use of bFGF and GDF-5 enhances the healing of medial collateral ligament injury, Biochem. Biophys. Res. Commun., 402(2):329-334 (2010).
Sanborn, T.J. et al., A Thermally Triggered, Enzymatically Cross-linked PEG-Peptide Hydrogel for Biomaterial Applications, Presented at 2001 Annual Meeting, Americal Institute of Chemical Engineers, Reno, NV, Nov. 4-9, 2001.
Scalfani, A.P. and Romo III., T., Injectable fillers for facial soft tissue enhancement, Facial Plast. Surg., 16(1):29-34 (2000).
Segers, V.F. and Lee, R.T., Local delivery of proteins and the use of self-assembling peptides, Drug Discov. Today, 12(13-14):561-8 (2007).
Segers, V.F.M. and Lee, R.T., Stem-cell therapy for cardiac disease, Nature 451, 937-942 (2008).
Segers, V.F.M. et al, Local delivery of protease-resistant stromal cell derived factor-1 for stem cell recruitment after myocardial infarction, Circulation, 116(15):1683-1692 (2007).
Semino, C.E. et al., Entrapment of migrating hippocampal neural cells in three-dimensional peptide nanofiber scaffold, Tissue Eng., 10(3-4):643-55 (2004).
Semino, C.E., Self-assembling peptides: from bio-inspired materials to bone regeneration, J. Dent Res., 87(7):606-616 (2008).
Serban, M.A. et al, Effects of extracellular matrix analogues on primary human fibroblast behavior, Acta Biomater., 4(1):67-75 (2008).
Shirai, K. et al, Multipotency of clonal cells derived from swine periodontal ligament and differential regulation by fibroblast growth factor and bone morphogenetic protein, J. Periodontal Res., 44(2):238-247 (2009).
Shivachar, A.C., Isolation and Culturing of Glial, Neuronal and Neural Stem Cell Types Encapsulated in Biodegradable Peptide Hydrogel, Topics in Tissue Engineering, vol. 4. Eds. N Ashammakhi, R Reis, & F Chiellini © 2008.
Song, H. et al, Hemostatic efficacy of biological self-assembling peptide nanofibers in a rat kidney model, Macromol Biosci., 10(1):33-39 (2010).
Spencer, N.J. et al, Peptide- and collagen-based hydrogel substrates for in vitro culture of chick cochleae, Biomaterials, 29(8):1028-1042 (2008).
Sur, S. et al, A hybrid nanofiber matrix to control the survival and maturation of brain neurons, Biomaterials, 33(2):545-55 (2012).
Takei, J., 3-Dimensional Cell Culture Scaffold For Everyone: Drug Screening, Tissue Engineering and Cancer Biology, AATEX, 11(3): 170-176 (2006).
Thonhoff, J.R. et al, Compatibility of human fetal neural stem cells with hydrogel biomaterials in vitro, Brain Res., 1187:42-51 (2008).
Tokunaga, M. et al, Implantation of cardiac progenitor cells using self-assembling peptide improves cardiac function after myocardial infarction, J. Mol. Cell. Cardiol., 49(6):972-983 (2010).
Tokunou, T. et al, Engineering insulin-like growth factor-1 for local delivery, FASEB J., 22(6):1886-1893 (2008).
Tortora, G. J., Principles of Human Anatomy, Fifth Edition, Chapter 4: The Integumentary System, 98-100 (1989).
Uemura, M. et al, Matrigel supports survival and neuronal differentiation of grafted embryonic stem cell-derived neural precursor cells, J. Neurosci. Res., 88(3):542-551 (2010).
Van Putten, S.M. et al, The downmodulation of the foreign body reaction by cytomegalovirus encoded interleukin-10, Biomaterials, 30(5):730-735 (2008).
Wang, Q.G. et al, The composition of hydrogels for cartilage tissue engineering can influence glycosaminoglycan profile, Eur. Cell Mater, 19:86-95 (2010).
Wang. T. et al, Molecular Mechanisms of RAD16-1 Peptide on Fast Stop Bleeding in Rat Models, Int. J. Mol. Sci., 13: 15279-15290 (2012).
Yamaoka, H. et al, Cartilage tissue engineering using human auricular chondrocytes embedded in different hydrogel materials, J. Biomed. Mater Res. A., 78(1):1-11 (2006).
Ye, Z. et al., Temperature and pH effects on biophysical and morphological properties of self-assembling peptide RADA16-I, J. Pept. Sci., 14(2):152-62 (2008).
Yla-Outinen, L. et al, Three-dimensional growth matrix for human embryonic stem cell-derived neuronal cells, J. Tissue Eng. Regen. Med., doi: 10.1002/term.1512 (2012).
Yokoi, H. et al., Dynamic reassembly of peptide RADA16 nanofiber scaffold, Proc. Natl. Acad. Sci. U S A, 102(24):8414-9 (2005).
Yoshimi, R. et al, Self-assembling peptide nanofiber scaffolds, platelet-rich plasma, and mesenchymal stem cells for injectable bone regeneration with tissue engineering, J. Craniofac. Surg., 20(5):1523-1530 (2009).
Yu, Y.C. et al., Construction of biologically active protein molecular architecture using self-assembling peptide-amphiphiles, Methods Enzymol., 289:571-87 (1997).
Zarzhitsky, S. and Rapaport, H., The interactions between doxorubicin and amphiphilic and acidic β-sheet peptides towards drug delivery hydrogels, J. Colloid Interface Sci. 360(2):525-531 (2011).
Zhang et al., Emerging Biological Materials Through Molecular Self-Assembly, Biotechnology Advances, 20: 321-339 (2002).
Zhang, S. et al, PuraMatrix: Self-Assembling Peptide Nanofiber Scaffolds, Scaffolding in Tissue Engineering, Chapter 15, 217-238 (1992).
Zhang, S. et al, Self-assembling peptides in biology, materials science and engineering, Peptide Science—Present and Future, 737-744 (1999).
Zhang, S. et al, Self-complementary oligopeptide matrices support mammalian cell attachment, Biomaterials, 16(18): 1385-1393 (1995).
Zhang, S. et al., Building from the bottom up, Materials Today, 20-27 (2003).
Zhang, S. Self-assembling peptide materials, Amino Acids, Pept. Proteins, 37:40-65 (2012).
Zhang, S. Beyond the Petri dish, Nat. Biotechnol., 22(2):151-2 (2004).
Zhang, S., Designer Self[ Assembling Peptide Nanofiber Scaffolds for Study of 3[D Cell Biology and Beyond, Cancer Research, 335-362 (2008).
Zhang, S., Fabrication of novel biomaterials through molecular self-assembly, Nat. Biotechnol., 21(10):1171-8 (2003).
Zhang, S., Hydrogels: Wet or let die, Nat. Mater., 3(1):7-8 (2004).
Zhao, X. et al., Recent development of peptide self-assembly, Progress in Natural Science 18, 6(10):653-660 (2008).
Zhaoyang, Y. et al., Temperature and pH effects on biophysical and morphological properties of self-assembling peptide RADA16-T, Journal of Peptide Science, 14(2):152-162 (2008).

\* cited by examiner (A)

(B)

(C)

(1): First layer
(2): Second layer 100 nm

SURFACTANT PEPTIDE NANOSTRUCTURES AND USES THEREOF IN DRUG DELIVERY

CROSS REFERENCE TO RELATED APPLICATIONS

This application claims the benefit of U.S. Provisional Patent Application No. 62/599,566, filed Dec. 15, 2017, the contents of which are hereby incorporated by reference herein in their entirety.

SEQUENCE LISTING

The instant application contains a Sequence Listing which has been filed electronically in ASCII format and is hereby incorporated by reference in its entirety. Said ASCII copy, created on December 19, is named 2004837-0223_SL.txt and is 29,335 bytes in size.

BACKGROUND

Surfactant peptides typically have a hydrophilic head group and a lipophilic tail having hydrophobic amino acids. Certain surfactant peptides have previously been disclosed (e.g., PCT Publication Numbers WO2003006043, WO2013181511, and WO2009018467). Some of the disclosed surfactant peptides are oligopeptides and di- and tri-block peptide copolymers with structures including a hydrophilic head group containing charged amino acids and a lipophilic tail containing hydrophobic amino acids in repeating units of 5 or more amino acids.

Other surfactant peptides, having a single repeating unit of four alanines, have been disclosed for use in stabilizing membrane proteins (e.g., US Patent Publication Number US20090069547).

SUMMARY

Previously disclosed surfactant peptides have been reported to self-assemble to form nanotubes having an average diameter of about 50 nM.

The present disclosure provides short surfactant peptides having a repeating hydrophobic unit of 4 or fewer amino acids that form nanospheric structures. Such nanospheric structures are particularly useful for formulation and delivery of therapeutic agents.

In some embodiments, the present disclosure provides compositions comprising peptides having repeating hydrophobic amino acids according to a formula of:

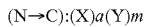 (N→C):(X)a(Y)m     Formula I

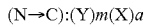 (N→C):(Y)m(X)a     Formula II

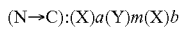 (N→C):(X)a(Y)m(X)b     Formula III

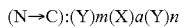 (N→C):(Y)m(X)a(Y)n     Formula IV

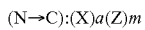 (N→C):(X)a(Z)m     Formula V

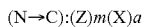 (N→C):(Z)m(X)a     Formula VI

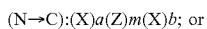 (N→C):(X)a(Z)m(X)b; or     Formula VII

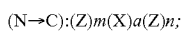 (N→C):(Z)m(X)a(Z)n;     Formula VIII wherein (X) is an amino acid having a nonpolar and noncharged sidechain at physiological pH;

(Y) is an amino acid having a cationic sidechain at physiological pH;

(Z) is an amino acid having an anionic sidechain at physiological pH; and wherein a is an integer equal to or less than 4;

b is an integer equal to or less than 4;

m is an integer equal to or greater than 1; and n is an integer equal to or greater than 1.

In some embodiments the peptide has a nanospheric structure. In some embodiments, the peptide forms a nanosphere. In some embodiments, the peptide forms a nanospheric structure with a center that is substantially free of self-assembling surfactant peptide. (e.g., a spherical nanovesicle).

In some embodiments, the amino acid of (X), (Y), and/or (Z) is a natural amino acid. In some embodiments, the amino acid of (X), (Y), and/or (Z) is a non-natural amino acid.

In some embodiments, the integer of a or b is 4. In some embodiments, the integer of a or b is 3.

In some embodiments, (X) is alanine, valine, leucine, isoleucine, methionine, phenylalanine, tryptophan, or glycine. In some embodiments, (X) is alanine. In some embodiments, (Y) is arginine, lysine, histidine, or ornithine. In some embodiments, (Y) is lysine. In some embodiments, (X) is alanine and (Y) is lysine. In some embodiments, (Z) is aspartatic acid or glutamic acid.

In some embodiments, one or more amino acids is an L-amino acid. In some embodiments, each amino acid is an L-amino acid. In some embodiments, one or more amino acids is a D-amino acid. In some embodiments, each amino acid is a D-amino acid.

In some embodiments, the peptide is 4-10 amino acids in length. In some embodiments, the peptide is 5 amino acids in length. In some embodiments, the peptide is 6 amino acids in length. In some embodiments, the peptide is 7 amino acids in length.

In some embodiments, the peptide comprises a modified N- and/or C-terminus. In some embodiments the peptide has an acetylated N-terminus and/or an aminated C-terminus.

In some embodiments, peptides have a nanospheric structure and an amino acid sequence according to any of SEQ ID NOs: 1-50. In some embodiments, peptides have a nanospheric structure and an amino acid sequence according to any one of SEQ ID NOs: 51-100.

In some embodiments, peptides have a nanospheric structure and an amino acid sequence of AAAK (SEQ ID NO:1). In some embodiments, peptides have a nanospheric structure and an amino acid sequence of AAAAK (SEQ ID NO: 5). In some embodiments, peptides have a nanospheric structure and an amino acid sequence of AAAKAAA (SEQ ID NO: 15).

In some embodiments, the disclosure provides compositions comprising nanospheric peptides in an aqueous solution. In some embodiments, the peptide is at a concentration of at least 0.01% (w/v). In some embodiments, the aqueous solution has a pH of from about 6 to about 8. In some embodiments the aqueous solution has a pH of about 7. In some embodiments, the aqueous solution is at an ionic strength of from about 0 M to about 0.3 M. In some embodiments, the aqueous solution is at an ionic strength of about 0.15 M. In some embodiments, the aqueous solution is isotonic.

In some embodiments, the disclosure provides compositions for use in drug delivery. In some embodiments, the compositions comprise an agent for delivery to a subject. In some embodiments, the agent is a therapeutic. In some embodiments, the agent is a drug (e.g., a small molecule). In some embodiments, the agent is a biologic. In some embodiments, the agent is an oligonucleotide. In some embodiments, the agent is an inhibitor of RNA. In some embodiments, the agent is an siRNA. In some embodiments, the agent is for delivery to a cancer cell.

In some embodiments, the disclosure provides methods for formulating an agent for delivery to a subject, comprising a step of contact the agent with a nanospheric peptide surfactant as described herein.

In some embodiments, the disclosure provides methods of delivering an agent to a subject, the method comprising administering to the subject a composition formulated with a peptide having repeating hydrophobic amino acids according to a formula of:

$$(N \rightarrow C):(X)a(Y)m \qquad \text{Formula I}$$

$$(N \rightarrow C):(Y)m(X)a \qquad \text{Formula II}$$

$$(N \rightarrow C):(X)a(Y)m(X)b \qquad \text{Formula III}$$

$$(N \rightarrow C):(Y)m(X)a(Y)n \qquad \text{Formula IV}$$

$$(N \rightarrow C):(X)a(Z)m \qquad \text{Formula V}$$

$$(N \rightarrow C):(Z)m(X)a \qquad \text{Formula VI}$$

$$(N \rightarrow C):(X)a(Z)m(X)b; \text{ or} \qquad \text{Formula VII}$$

$$(N \rightarrow C):(Z)m(X)a(Z)n; \qquad \text{Formula VIII}$$

wherein (X) is an amino acid having a nonpolar and noncharged sidechain at physiological pH;
(Y) is an amino acid having a cationic sidechain at physiological pH;
(Z) is an amino acid having an anionic sidechain at physiological pH; and wherein
a is an integer equal to or less than 4;
b is an integer equal to or less than 4;
m is an integer equal to or greater than 1; and
n is an integer equal to or greater than 1.

In some embodiments, the peptide forms a nanospheric structure. In some embodiments, the peptide forms a nanosphere. In some embodiments, the peptide forms a spherical nanovesicle.

In some embodiments, the amino acid of (X), (Y), and/or (Z) is a natural amino acid. In some embodiments, the amino acid of (X), (Y), and/or (Z) is a non-natural amino acid.

In some embodiments, the integer of a or b is 4. In some embodiments, the integer of a or b is 3.

In some embodiments, (X) is alanine, valine, leucine, isoleucine, methionine, phenylalanine, tryptophan, or glycine. In some embodiments, (X) is alanine. In some embodiments, (Y) is arginine, lysine, histidine, or ornithine. In some embodiments, (Y) is lysine. In some embodiments, (X) is alanine and (Y) is lysine. In some embodiments, (Z) is aspartic acid or glutamic acid.

In some embodiments, one or more amino acids is an L-amino acid. In some embodiments, each amino acid is an L-amino acid. In some embodiments, one or more amino acids is a D-amino acid. In some embodiments, each amino acid is a D-amino acid.

In some embodiments, the peptide is 4-10 amino acids in length. In some embodiments, the peptide is 5 amino acids in length. In some embodiments, the peptide is 6 amino acids in length. In some embodiments, the peptide is 7 amino acids in length.

In some embodiments, the peptide comprises a modified N- and/or C-terminus. In some embodiments the peptide has an acetylated N-terminus and/or an aminated C-terminus.

In some embodiments, peptides have a nanospheric structure and an amino acid sequence according to any of SEQ ID NOs: 1-50. In some embodiments, peptides have a nanospheric structure and an amino acid sequence according to any one of SEQ ID NOs: 51-100.

In some embodiments, peptides have a nanospheric structure and an amino acid sequence of AAAK (SEQ ID NO:1). In some embodiments, peptides have a nanospheric structure and an amino acid sequence of AAAAK (SEQ ID NO: 5). In some embodiments, peptides have a nanospheric structure and an amino acid sequence of AAAKAAA (SEQ ID NO: 15).

In some embodiments, the disclosure provides compositions comprising nanospheric peptides in an aqueous solution. In some embodiments, the peptide is at a concentration of at least 0.01% (w/v). In some embodiments, the aqueous solution has a pH of from about 6 to about 8. In some embodiments the aqueous solution has a pH of about 7. In some embodiments, the aqueous solution is at an ionic strength of from about 0 M to about 0.3 M. In some embodiments, the aqueous solution is at an ionic strength of about 0.15 M. In some embodiments, the aqueous solution is isotonic.

DEFINITIONS

In order for the present disclosure to be more readily understood, certain terms are first defined below. Additional definitions for the following terms and other terms are set forth throughout the specification.

The term "agent" as used herein refers to a compound or entity of any chemical class including, for example, polypeptides, nucleic acids, saccharides, lipids, small molecules, metals, or combinations thereof. In some embodiments, an agent is or comprises a natural product in that it is found in and/or is obtained from nature. In some embodiments, an agent is or comprises one or more entities that are man-made in that it is designed, engineered, and/or produced through action of the hand of man and/or is not found in nature. In some embodiments, an agent may be utilized in isolated or pure form; in some embodiments, an agent may be utilized in crude form. Some particular agents that may be utilized in accordance with the present invention include small molecules, antibodies, antibody fragments, aptamers, nucleic acids (e.g., siRNAs, shRNAs, DNA/RNA hybrids, antisense oligonucleotides, and ribozymes), peptides, peptide mimetics, etc. In some embodiments, an agent is or comprises a polymer. In some embodiments, an agent is not a polymer and/or is substantially free of any polymer. In some embodiments, an agent contains at least one polymeric moiety. In some embodiments, an agent lacks or is substantially free of any polymeric moiety. In some embodiments, an agent is or comprises a cellular lysate.

As used herein, the term "amino acid," in its broadest sense, refers to any compound and/or substance that can be incorporated into a polypeptide chain, e.g., through formation of one or more peptide bonds. In some embodiments, an amino acid has the general structure $H_2N-C(H)(R)-COOH$. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, and/or substitution as compared with the general structure. As will be clear from context, in some embodiments, the term "amino acid" is used to refer to a free amino acid; in some embodiments it is used to refer to an amino acid residue of a polypeptide.

As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Two events or entities are "associated" with one another, as that term is used herein, if the presence, level and/or form of one is correlated with that of the other. In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

The term "comparable" is used herein to describe two (or more) sets of conditions, circumstances, individuals, or populations that are sufficiently similar to one another to permit comparison of results obtained or phenomena observed. In some embodiments, comparable sets of conditions, circumstances, individuals, or populations are characterized by a plurality of substantially identical features and one or a small number of varied features. Those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied. Those skilled in the art will appreciate that relative language used herein (e.g., enhanced, activated, reduced, inhibited, etc.) will typically refer to comparisons made under comparable conditions.

By "complementary" is meant capable of forming ionic or hydrogen bonding interactions between hydrophilic residues from adjacent peptides, e.g., in a sheet or scaffold, each hydrophilic residue in a peptide either hydrogen bonds or ionically pairs with a hydrophilic residue on an adjacent peptide or is exposed to solvent.

Certain methodologies may include a step of "determining". Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

The term "in vitro" as used herein refers to events that occur in an artificial environment, e.g., in a test tube or reaction vessel, in cell culture, etc., rather than within a multi-cellular organism.

The term "in vivo" as used herein refers to events that occur within a multi-cellular organism, such as a human and a non-human animal. In the context of cell-based systems, the term may be used to refer to events that occur within a living cell (as opposed to, for example, in vitro systems).

As used herein, the term "nanospheric" refers to spherical structures having a diameter in the nanometer range. As used herein, a "nanospheric structure" includes nanospheres and/or spherical nanovesicles. A spherical nanovesicle is similar to a nanosphere but has a center that is substantially free of self-assembling surfactant peptide.

The term "peptide" as used herein refers to any polymeric chain of amino acids. In some embodiments, a peptide has an amino acid sequence that occurs in nature. In some embodiments, a peptide has an amino acid sequence that does not occur in nature. In some embodiments, a peptide has an amino acid sequence that is engineered in that it is designed and/or produced through action of the hand of man. In some embodiments, a peptide comprises or consists of natural amino acids, non-natural amino acids, or both. In some embodiments, a peptide comprises or consists of only natural amino acids or only non-natural amino acids. In some embodiments, a peptide comprises D-amino acids, L-amino acids, or both. In some embodiments, a peptide comprises only D-amino acids. In some embodiments, a peptide comprises only L-amino acids. In some embodiments, a peptide includes one or more pendant groups or other modifications, e.g., modifying or attached to one or more amino acid side chains, at the peptide's N-terminus, at the peptide's C-terminus, or any combination thereof. In some embodiments, such pendant groups or modifications are selected from acetylation, amidation, lipidation, methylation, pegylation, etc., including combinations thereof. In some embodiments, the term "peptide" may be appended to a name of a reference peptide, activity, or structure; in such instances it is used herein to refer to peptides that share the relevant activity or structure and thus can be considered to be members of the same class or family of peptides. For each such class, the present specification provides and/or those skilled in the art will be aware of exemplary peptides within the class whose amino acid sequences and/or functions are known; in some embodiments, such exemplary peptides are reference peptides for the peptide class or family. In some embodiments, a member of a peptide class or family shows significant sequence homology or identity with, shares a common sequence motif (e.g., a characteristic sequence element) with, and/or shares a common activity (in some embodiments at a comparable level or within a designated range) with a reference peptide of the class; in some embodiments with all peptides within the class.

The term "pure" is used to indicate the extent to which the peptides described herein are free of other chemical species, including deletion adducts of the peptide and peptides of differing lengths.

The term "reference" as used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

The term "self-assembling" is used herein in reference to certain peptides that, under appropriate conditions, can spontaneously self-associate into structures in solution (e.g., aqueous solutions), such as, nanospheric structures including nanospheres and spherical nanovesicles. In some embodiments, self-assembly (and/or dis-assembly) into nanospheric structures is responsive to one or more environmental triggers (e.g., change in one or more of pH, temperature, ionic strength, osmolarity, osmolality, applied pressure, applied shear stress, etc.). In some embodiments, compositions of self-assembling polypeptides are characterized by detectable nanospheric structure when the polypeptides are in an assembled state.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

As used herein, a "therapeutically effective amount" is an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

Unless defined otherwise, technical and scientific terms have the same meaning as commonly understood by one of ordinary skill in the art to which this invention belongs.

BRIEF DESCRIPTION OF THE DRAWINGS

The following figures are for illustration purposes only, not for limitation.

In FIG. 7A, Nanotubes formed by typical surfactant peptides whose number of repeating hydrophobic amino acids is equal to 5 or more (e.g., Ac-A6K-NH$_2$ (SEQ ID NO:105)). In FIG. 7B, Nanospheric structure of surfactant peptides disclosed herein whose number of repeating hydrophobic amino acids is 3 or 4 (e.g., Ac-A3KA3-NH$_2$ (SEQ ID NO:65) and Ac-A4K-NH$_2$ (SEQ ID NO:55)).

FIGS. 11A and 11B depict the data from Method 1 and Method 2, respectively.

FIGS. 12A-C show luciferase emission from the control samples (e.g., mock, Dhrama-siRNA, Dhrama-NC siRNA, the peptide/NC-siRNA complex samples), the peptide/siRNA complex samples. FIGS. 12A and 12B represent the result from Method 1. FIG. 12C shows the result from Method 2. FIGS. 12D (Method 1) and 12E (Method 2) depict the suppression percentage of luciferase emission. Each luciferase emission data from the peptide/siRNA complexes has been normalized by the corresponding luciferase emission data from the peptide/NC siRNA complexes.

DETAILED DESCRIPTION

Figure 1:
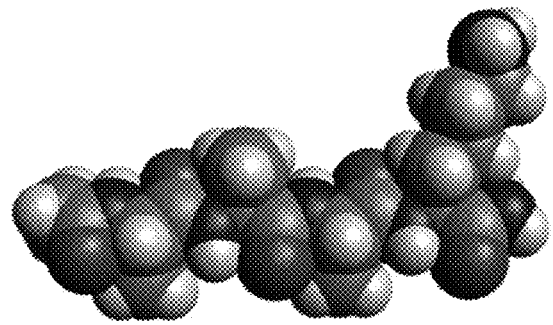
FIG. 1 depicts molecular models of exemplary surfactant peptides; (A) Ac-A3K-NH$_2$ (SEQ ID NO:51), (B) Ac-A4K-NH$_2$ (SEQ ID NO:55), (C) Ac-A3KA3-NH$_2$ (SEQ ID NO:65). Ac-A3K-NH$_2$ (SEQ ID NO:51) and Ac-A4K-NH$_2$ (SEQ ID NO:55) have one short hydrophobic leg. Ac-A3KA3-NH$_2$ (SEQ ID NO:55) has two short hydrophobic legs.
Figure 1:
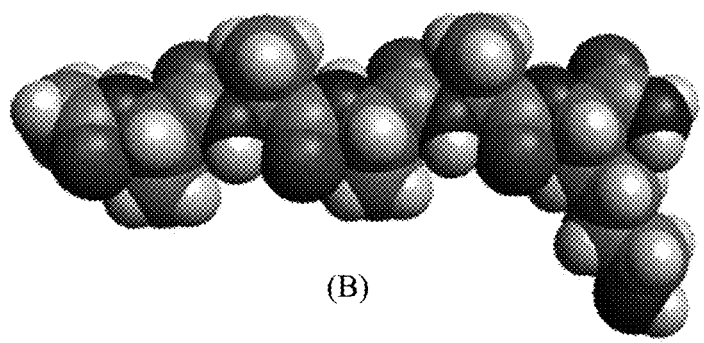
Figure 1:
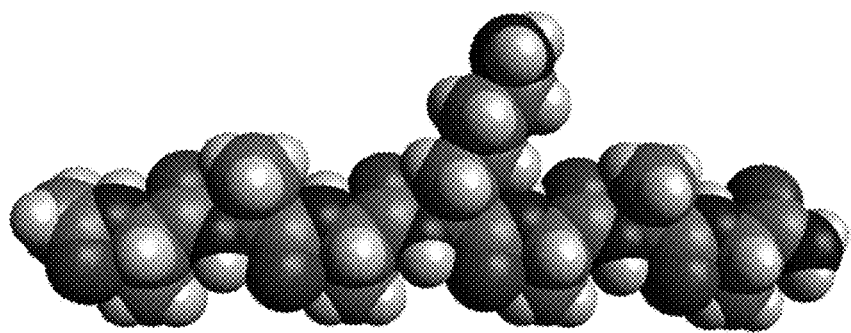
Figure 2:
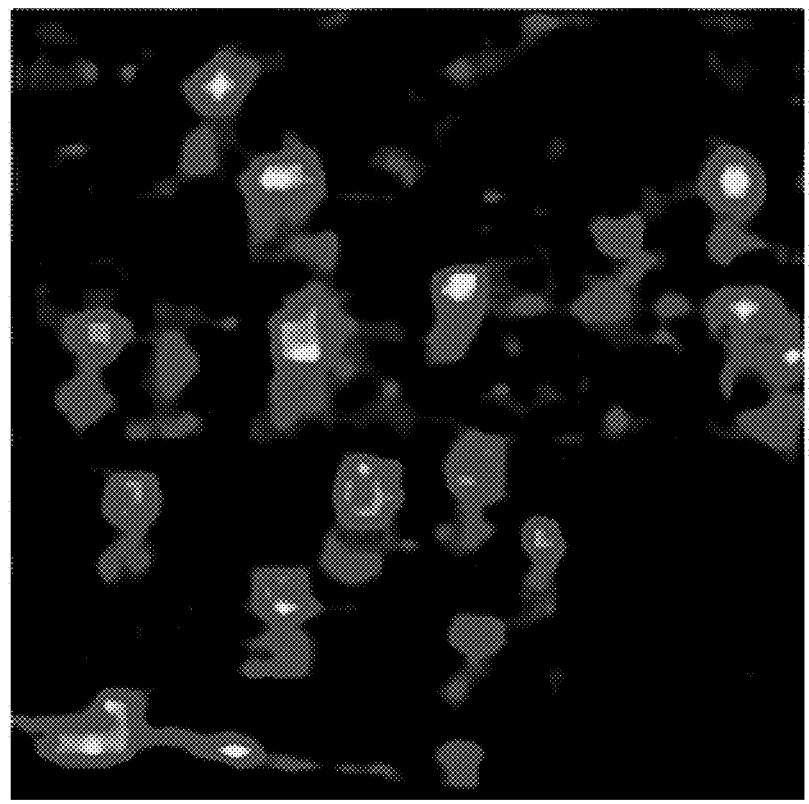
FIG. 2 shows an AFM image of Ac-A6K-NH$_2$ (SEQ ID NO: 105) which has the typical nanotube structure of a conventional surfactant peptide.
Figure 3A:
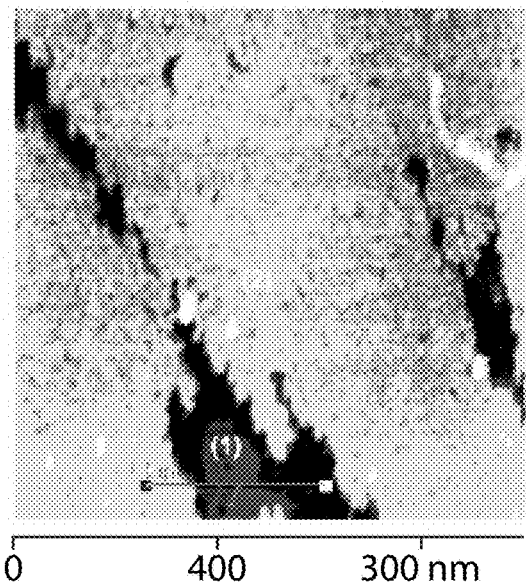
FIGS. 3A-3C show an AFM image of a double layer structure of Ac-A6K-NH$_2$ (SEQ ID NO: 105) at 0.1% (w/v). The thickness of each layer is 0.8 nm. Ac-A6K-NH$_2$ (SEQ ID NO: 105) formed a double layer structure at 0.1% (w/v).
Figure 3B:
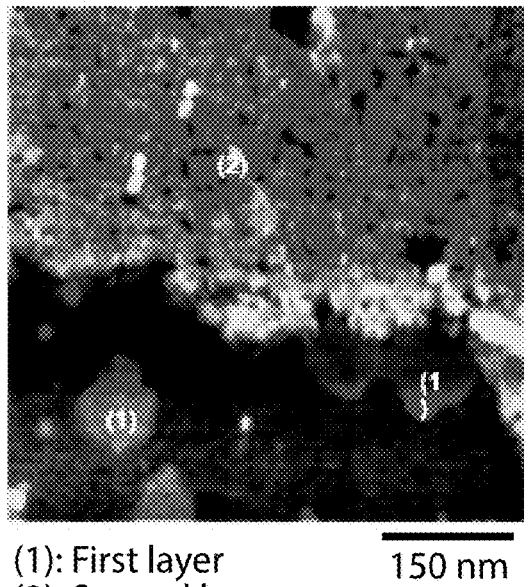
Figure 3C:
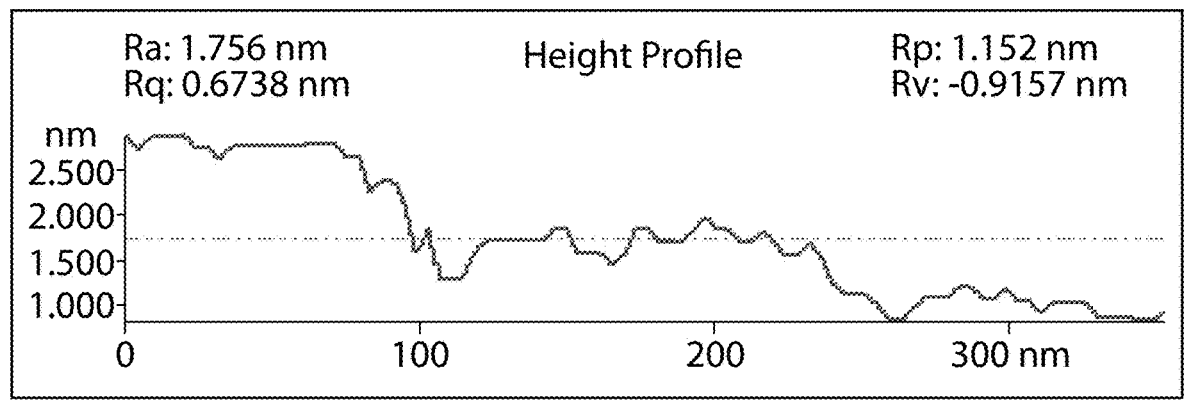

The present disclosure relates to surfactant peptides nanostructures and their use in delivery of agents to subjects. The present disclosure encompasses the discovery that certain surfactant peptides having hydrophobic amino acid repeats of four or fewer amino acids form nanospheric structures that are well suited for delivery of agents.

Among other things, the present disclosure identifies a shortcoming of surfactant peptides that have five or more hydrophobic amino acid repeats, in particular that they tend to form nanotube structures rather than nanospheric structures (nanosphere or spherical nanovesicle). Moreover, they tend to aggregate when complexed with agents for delivery such as siRNA. The present disclosure provides nanospheric structures that are better suited for delivery of agents to subjects, in particular siRNA or other therapeutics.

Peptides

The present disclosure provides surfactant peptide nanostructures having a small number (i.e., an integer equal to or less than four) of repeating hydrophobic amino acids. In some embodiments, peptides are provided having according to Formula I, II, III, IV, V, VI, VII, or VIII below:

(N→C):(X)a(Y)m      Formula I (N→C):(Y)m(X)a      Formula II (N→C):(X)a(Y)m(X)b      Formula III (N→C):(Y)m(X)a(Y)n      Formula IV (N→C):(X)a(Z)m      Formula V (N→C):(Z)m(X)a      Formula VI (N→C):(X)a(Z)m(X)b      Formula VII (N→C):(Z)m(X)a(Z)n;      Formula VIII wherein (X) is an amino acid having a nonpolar and noncharged sidechain at physiological pH;

(Y) is an amino acid having a cationic sidechain at physiological pH;

(Z) is an amino acid having an anionic sidechain at physiological pH; and wherein a is an integer equal to or less than 4;

b is an integer equal to or less than 4;

m is an integer equal to or greater than 1; and n is an integer equal to or greater than 1.

In some embodiments, the amino acid of (X), (Y), and/or (Z) is a natural amino acid. In some embodiments, the amino acid of (X), (Y), and/or (Z) is a non-natural amino acid. In some embodiments, (X) is alanine, valine, leucine, isoleucine, methionine, phenylalanine, tryptophan, or glycine. In some embodiments, (Y) is arginine, lysine, histidine, or ornithine. In some embodiments, (X) is arginine and (Y) is lysine. In some embodiments, (Z) is aspartic acid or glutamic acid. The amino acids of (X), (Y) and/or (Z) may be L-amino acids, D-amino acids, or combinations thereof.

In some embodiments the number of hydrophobic repeating amino acids is four. In some embodiments, the number of hydrophobic repeating amino acids is three. In some embodiments, the number of hydrophobic repeating amino acids is two.

In some embodiments, the total number of amino acids in the peptide is from about 4 to about 10. In some embodiments, the total number of amino acids in the peptide is 4, 5, 6, 7, 8, 9, or 10.

The amino acid sequence of exemplary peptide structures is provided in Table 1.

TABLE 1

Exemplary surfactant peptides.

| SEQ ID NO | Name | Sequence | Number of residues |
|---|---|---|---|
| 1 | A3K | AAAK | 4 |
| 2 | KA3 | KAAA | 4 |
| 3 | V3K | VVVK | 4 |
| 4 | KV3 | KVVV | 4 |
| 5 | A4K | AAAAK | 5 |
| 6 | KA4 | KAAAA | 5 |
| 7 | V4K | VVVVK | 5 |
| 8 | KV4 | KVVVV | 5 |
| 9 | A3KA | AAAKA | 5 |
| 10 | AKA3 | AKAAA | 5 |
| 11 | A3KA2 | AAAKAA | 6 |
| 12 | A2KA3 | AAKAAA | 6 |

TABLE 1-continued

Exemplary surfactant peptides.

| SEQ ID NO | Name | Sequence | Number of residues |
|---|---|---|---|
| 13 | A4KA | AAAAKA | 6 |
| 14 | AKA4 | AKAAAA | 6 |
| 15 | A3KA3 | AAAKAAA | 7 |
| 16 | V3KV3 | VVVKVVV | 7 |
| 17 | A4KA2 | AAAAKAA | 7 |
| 18 | A3K2A3 | AAAKKAAA | 8 |
| 19 | V3K2V3 | VVVKKVVV | 8 |
| 20 | A4KA3 | AAAAKAAA | 8 |
| 21 | V4KV3 | VVVVKVVV | 8 |
| 22 | A4KA4 | AAAAKAAAA | 9 |
| 23 | V4KV4 | VVVVKVVVV | 9 |
| 24 | A4K2A4 | AAAAKKAAAA | 10 |
| 25 | V3K2V4 | VVVKKVVVV | 10 |
| 26 | A3D | AAAD | 4 |
| 27 | DA3 | DAAA | 4 |
| 28 | V3D | VVVD | 4 |
| 29 | DV3 | DVVV | 4 |
| 30 | A4D | AAAAD | 5 |
| 31 | DA4 | DAAAA | 5 |
| 32 | V4D | VVVVD | 5 |
| 33 | DV4 | DVVVV | 5 |
| 34 | A3DA | AAADA | 5 |
| 35 | ADA3 | ADAAA | 5 |
| 36 | A3DA2 | AAADAA | 6 |
| 37 | A2DA3 | AADAAA | 6 |
| 38 | A4DA | AAAADA | 6 |
| 39 | ADA4 | ADAAAA | 6 |
| 40 | A3DA3 | AAADAAA | 7 |
| 41 | V3DV3 | VVVDVVV | 7 |

In some embodiments, the peptide has an acetylated N-terminus and/or an aminated C-terminus. Exemplary peptides having an acetylated N-terminus and/or an aminated C-terminus are shown in Table 2.

TABLE 2

Exemplary surfactant peptides with aminated C-termini and acetylated N-termini.

| SEQ ID NO | Name | Sequence | Number of residues |
|---|---|---|---|
| 51 | Ac-A3K-NH$_2$ | Ac-AAAK-NH$_2$ | 4 |
| 52 | Ac-KA3-NH$_2$ | Ac-KAAA-NH$_2$ | 4 |
| 53 | Ac-V3K-NH$_2$ | Ac-VVVK-NH$_2$ | 4 |
| 54 | Ac-KV3-NH$_2$ | Ac-KVVV-NH$_2$ | 4 |
| 55 | Ac-A4K-NH$_2$ | Ac-AAAAK-NH$_2$ | 5 |
| 56 | Ac-KA4-NH$_2$ | Ac-KAAAA-NH$_2$ | 5 |
| 57 | Ac-V4K-NH$_2$ | Ac-VVVVK-NH$_2$ | 5 |
| 58 | Ac-KV4-NH$_2$ | Ac-KVVVV-NH$_2$ | 5 |
| 59 | Ac-A3KA-NH$_2$ | Ac-AAAKA-NH$_2$ | 5 |
| 60 | Ac-AKA3-NH2 | Ac-AKAAA-NH$_2$ | 5 |
| 61 | Ac-A3KA2-NH2 | Ac-AAAKAA-NH$_2$ | 6 |
| 62 | Ac-A2KA3-NH2 | Ac-AAKAAA-NH$_2$ | 6 |
| 63 | Ac-A4KA-NH2 | Ac-AAAAKA-NH$_2$ | 6 |
| 64 | Ac-AKA4-NH2 | Ac-AKAAAA-NH$_2$ | 6 |
| 65 | Ac-A3KA3-NH2 | Ac-AAAKAAA-NH$_2$ | 7 |
| 66 | Ac-V3KV3-NH$_2$ | Ac-VVVKVVV-NH$_2$ | 7 |
| 67 | Ac-A4KA2-NH$_2$ | Ac-AAAAKAA-NH$_2$ | 7 |
| 68 | Ac-A3K2A3-NH$_2$ | Ac-AAAKKAAA-NH$_2$ | 8 |
| 69 | Ac-V3K2V3-NH$_2$ | Ac-VVVKKVVV-NH$_2$ | 8 |
| 70 | Ac-A4KA3-NH$_2$ | Ac-AAAAKAAA-NH$_2$ | 8 |
| 71 | Ac-V4KV3-NH$^2$ | Ac-VVVVKVVV-NH$_2$ | 8 |
| 72 | Ac-A4KA4-NH$_2$ | Ac-AAAAKAAAA-NH$_2$ | 9 |
| 73 | Ac-V4KV4-NH$_2$ | Ac-VVVVKVVVV-NH$_2$ | 9 |
| 74 | Ac-A4K2A4-NH$_2$ | Ac-AAAAKKAAAA-NH$_2$ | 10 |
| 75 | Ac-V3K2V4-NH$_2$ | Ac-VVVKKVVVV-NH$_2$ | 10 |
| 76 | Ac-A3D-NH$_2$ | Ac-AAAD-NH$_2$ | 4 |
| 77 | Ac-DA3-NH$_2$ | Ac-DAAA-NH$_2$ | 4 |
| 78 | Ac-V3D-NH$_2$ | Ac-VVVD-NH$_2$ | 4 |
| 79 | Ac-DV3-NH$_2$ | Ac-DVVV-NH$_2$ | 4 |
| 80 | Ac-A4D-NH$_2$ | Ac-AAAAD-NH$_2$ | 5 |
| 81 | Ac-DA4-NH$_2$ | Ac-DAAAA-NH$_2$ | 5 |
| 82 | Ac-V4D-NH$_2$ | Ac-VVVVD-NH$_2$ | 5 |
| 83 | Ac-DV4-NH$_2$ | Ac-DVVVV-NH$_2$ | 5 |
| 84 | Ac-A3DA-NH$_2$ | Ac-AAADA-NH$_2$ | 5 |
| 85 | Ac-ADA3-NH$_2$ | Ac-ADAAA-NH$_2$ | 5 |
| 86 | Ac-A3DA2-NH$_2$ | Ac-AAADAA-NH$_2$ | 6 |
| 87 | Ac-A2DA3-NH$_2$ | Ac-AADAAA-NH$_2$ | 6 |

TABLE 2-continued

Exemplary surfactant peptides with aminated
C-termini and acetylated N-termini.

| SEQ ID NO | Name | Sequence | Number of residues |
|---|---|---|---|
| 88 | Ac-A4DA-NH$_2$ | Ac-AAAADA-NH$_2$ | 6 |
| 89 | Ac-ADA4-NH$_2$ | Ac-ADAAAA-NH$_2$ | 6 |
| 90 | Ac-A3DA3-NH$_2$ | Ac-AAADAAA-NH$_2$ | 7 |
| 91 | Ac-V3DV3-NH$_2$ | Ac-VVVDVVV-NH$_2$ | 7 |

Nanostructure

In some embodiments, surfactant peptides assemble to form for nanospheric structures. As used herein, nanospheric structures include structures comprising a nanosphere and/or a spherical nanovesicle. A spherical nanovesicle is similar to a nanosphere but has a center that is substantially free of self-assembling surfactant peptide.

Nanostructure plays an important role in formulation of agents (e.g., therapeutics, such as siRNA). Atomic force microscope (AFM) studies show that surfactant peptides having five or more repeating hydrophobic amino acids typically form nanotubes or double layers, as opposed to more desirable nanospheric structures. In contrast, surfactant peptides having four or fewer repeating hydrophobic amino acids were found to form nanospheric structures (e.g., spherical nanovesicles).

Figure 4:
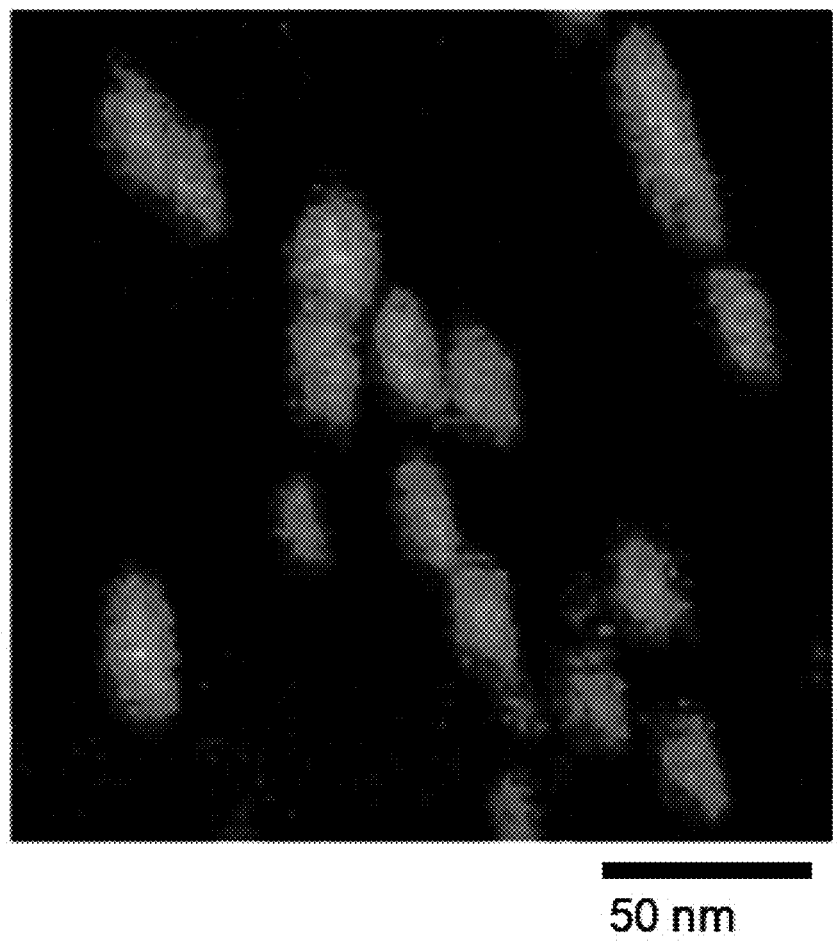
FIG. 4 shows an AFM image of Ac-A3K-NH$_2$ (SEQ ID NO:51). Ac-A3K-NH$_2$ (SEQ ID NO:51) forms nanospheres at 0.1% (w/v). The diameter of the nanospheres is 28 nm.

It has been previously reported that the nanostructure of A3K (SEQ ID NO:1) is a double layered membrane (*J. Phys. Chem. B*, 2014, 118 (42), pp 12215-12222). A3K (SEQ ID NO:1) has been also been reported to have nanostructures as loose peptide stacks. It has been studied for potential antibacterial capacity (*Biomacromolecules*, 2010, 11 (2), pp 402-411). In another report, A3K (SEQ ID NO:1), A6K (SEQ ID NO:101), and A9K (SEQ ID NO:102) were tested for interactions with lipid membranes. (RSC Adv., 2017, 7, 35973). However, unlike as reported in the references above, under appropriate conditions A3K (SEQ ID NO:1) can form nanospheric structures as shown in FIG. 4.

Figure 5A:
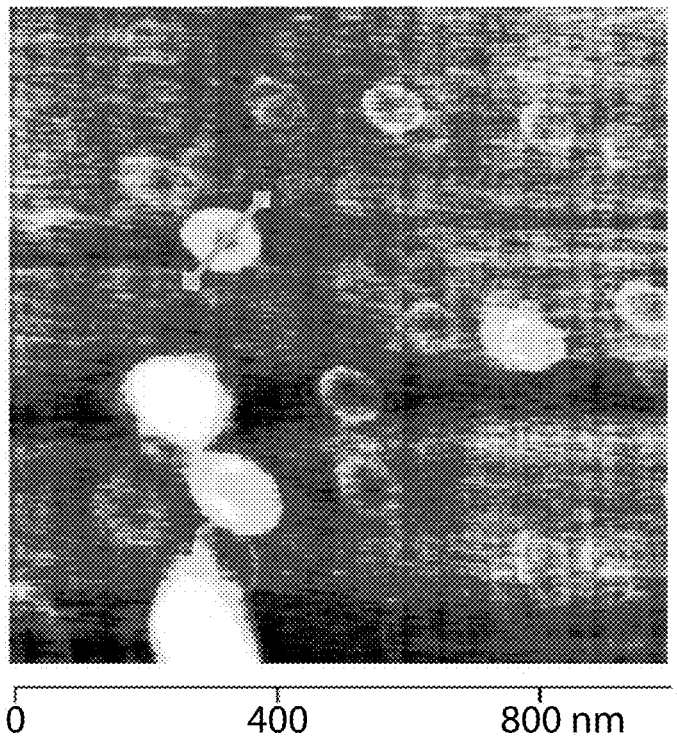
FIGS. 5A-5B show an AFM image of Ac-A4K-NH$_2$ (SEQ ID NO:55). Ac-A4K-NH$_2$ (SEQ ID NO:55) forms nanospheres (i.e., spherical nanovesicles). The diameter of the nanospheres is 85 nm. The height profile exhibits that the edge of the nanospheres dried on the mica surface have a higher height than their middle section. This indicates that the insides of A4K (SEQ ID NO:55) nanospheres are void (i.e., forming spherical nanovesicles).
Figure 5B:
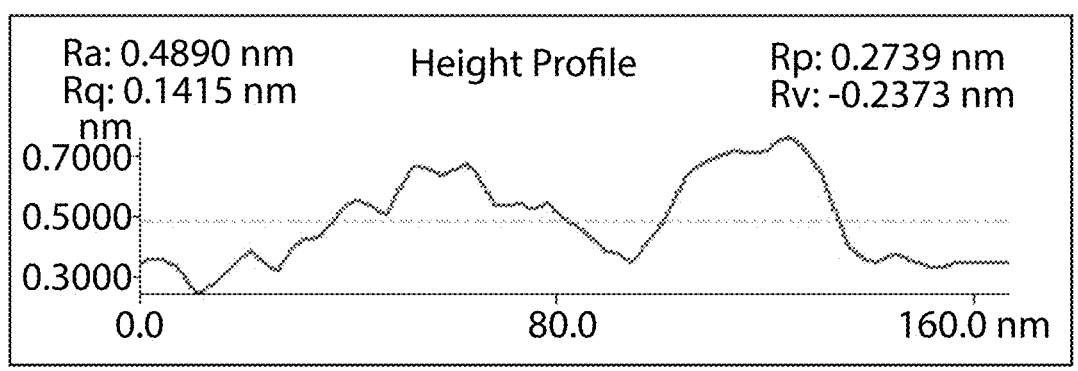

It has been previously reported that A4K (SEQ ID NO:5) is highly water soluble and does not exhibit relevant self-assembly in water, unlike A6K which shows self-assembly to form nanotubes. (*Langmuir*, 2014, 30 (33), pp 10072-10079). However, in contrast what has previously been reported, it is demonstrated herein that under appropriate conditions A4K (SEQ ID NO:5) can form nanospheric structures (spherical nanovesicles) in water as shown in FIG. 5.

Figure 6A:
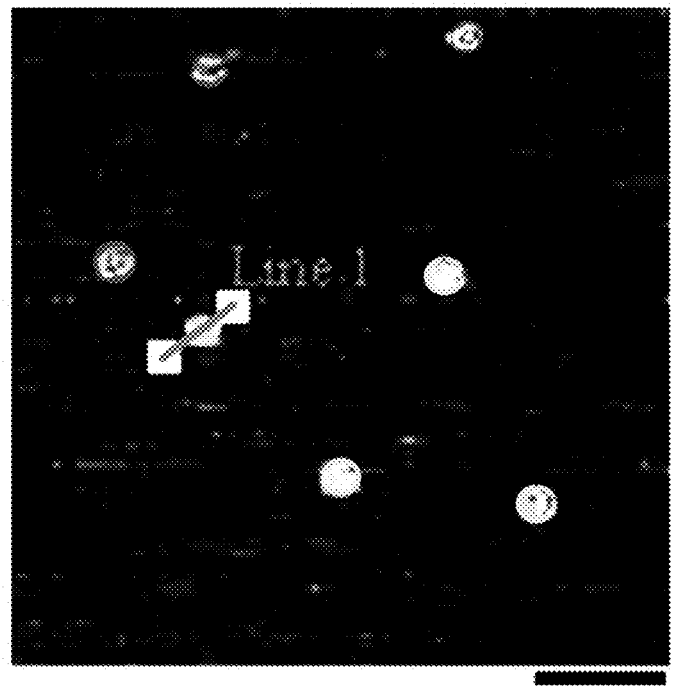
FIGS. 6A-6B show an AFM image of Ac-A3KA3-NH$_2$ (SEQ ID NO:65). Ac-A3KA3-NH$_2$ (SEQ ID NO:65) forms nanospheres (i.e., spherical nanovesicles). The diameter of the nanospheres is 30 nm. The height profile exhibits that the edge of the nanospheres dried on the mica surface have a higher height than their middle section. This indicates that the insides of Ac-A3KA3-NH$_2$ (SEQ ID NO:65) nanospheres are void (i.e., forming spherical nanovesicles).
Figure 6B:
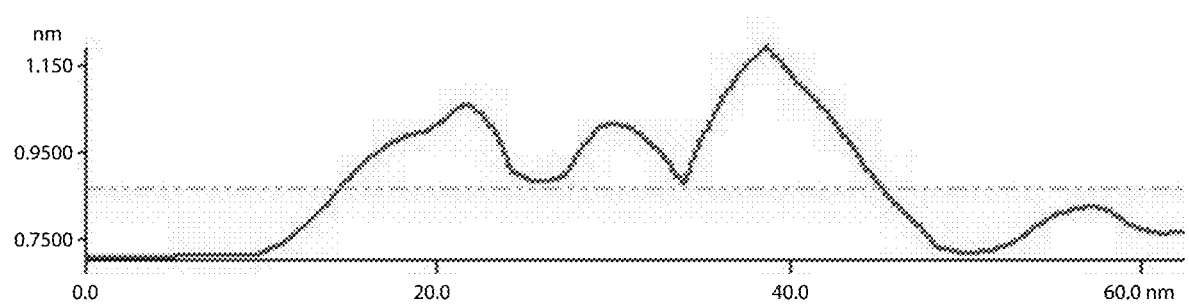
Figure 7A:
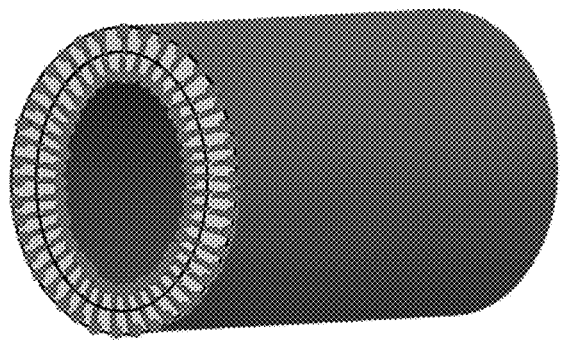
FIGS. 7A and 7B illustrate the nanostructure of surfactant peptides.
Figure 7B:
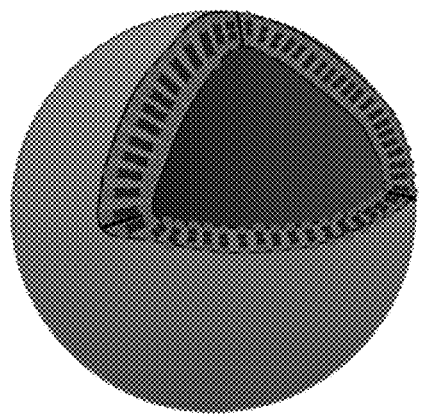
Figure 8:
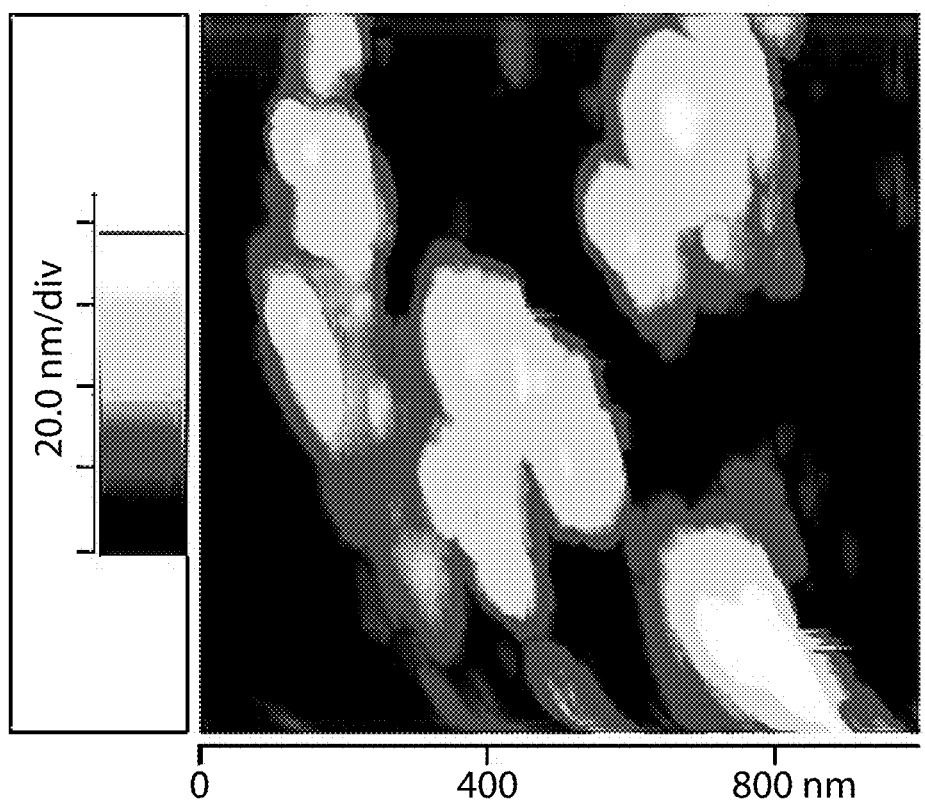
FIG. 8 shows an AFM image of an A6K/siRNA complex (0.1%/0.01%). The A6K/siRNA complex aggregates.
Figure 9A:
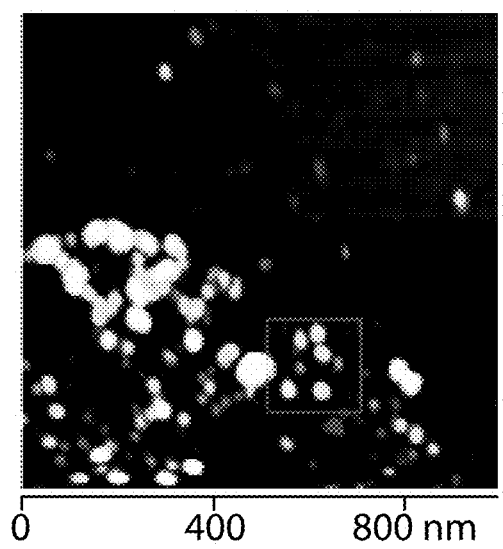
FIGS. 9A-9B show an AFM image of Ac-A4K-NH$_2$ (SEQ ID NO:55)/siRNA complex (0.1%/0.01%). The Ac-A4K-NH$_2$ (SEQ ID NO:55)/siRNA complex forms nanospheric structures.
Figure 9B:
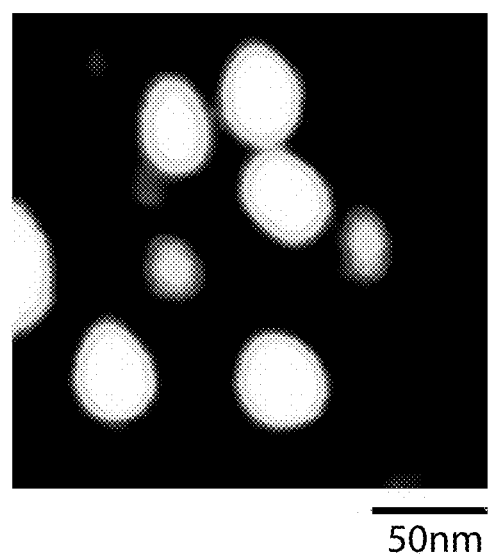
Figure 10A:
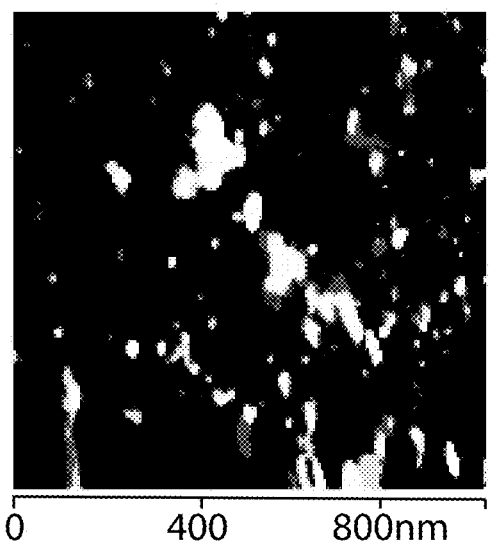
FIG. 10 shows an AFM image of Ac-A3KA3-NH$_2$ (SEQ ID NO:65)/siRNA complex (0.5%/0.05%). The Ac-A3KA3-NH$_2$ (SEQ ID NO:65)/siRNA complex forms nanospheric structures.
Figure 10B:
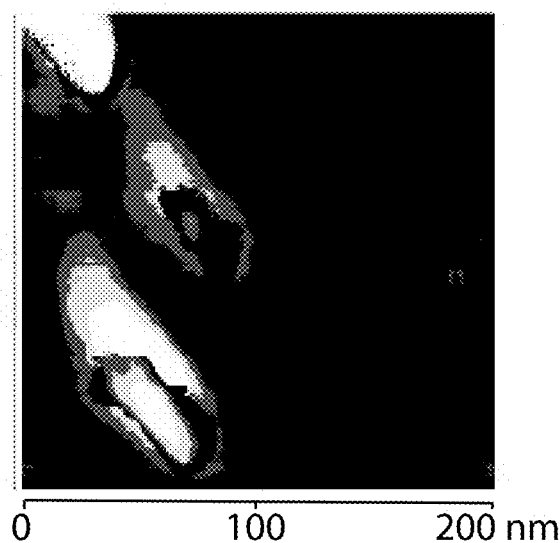

A3KA3 (SEQ ID NO:15) has previously been used as a test compound for optimization of electrospray ionization condition. (Rapid Commun Mass Spectrom. 2017, 31(13): 1129-1136). However, nanostructures of A3KA3 (SEQ ID NO:15) have not been described in the reference above. It is demonstrated herein that under appropriate conditions, A3KA3 (SEQ ID NO:15) can undergo self-assembly to form nanospheric structures (spherical nanovesicles) as shown in FIG. 6.

The present disclosure demonstrates the superior properties of surfactant peptides disclosed herein. Results of an experiment in which the peptides were complexed with siRNA in an aqueous solution at pH 7.5 are shown in Table 3. The peptides AAAK (SEQ ID NO: 1), AAAAK (SEQ ID NO: 5), and AAAKAAA (SEQ ID NO: 15), at peptide concentrations of 0.1% (w/v) and 0.5% (w/v), when mixed with siRNA at concentrations of 0.01% (w/v) and 0.05% (w/v), were found in a transmittance study to be transparent and substantially without phase separation. In contrast, under similar conditions, AAAAAK (SEQ ID NO: 101) and AAAAAAK (SEQ ID NO: 102) became cloudy and phase separated (see results in Table 3).

TABLE 3

Transmittance results of surfactant peptides and surfactant peptide/siRNA complexes in aqueous solution at pH 7.5.

| | Transmittance (%) | | | |
|---|---|---|---|---|
| | Peptide alone | | With siRNA | |
| | 0.1% | 0.5% | (peptide %/siRNA %) | |
| Surfactant peptides | (w/v) | (w/v) | 0.1%/0.01% | 0.5%/0.05% |
| A3K (SEQ ID NO: 1) | 96.2 | 99.6 | 81.1 | 77.3 |
| A4K (SEQ ID NO: 5) | 99.4 | 97.8 | 98.7 | 97.5 |
| A3KA3 (SEQ ID NO: 15) | 99.2 | 97.5 | 98.7 | 88.2 |
| A5K# (SEQ ID NO: 103) | 99.2 | 71.9 | 95.5 | 22.7* |
| A6K# (SEQ ID NO: 101) | 94.8 | 98.7 | 38.4* | 15.3* |
| A6K2A6# (SEQ ID NO: 104) | 98.5 | 83.1 | 62.9* | 12.7* | exemplary conventional self-assembling peptides for comparison
*significantly cloudy and phase-separated.

Compositions

Surfactant peptides with equal to or fewer than four repeating hydrophobic amino acids can be formulated with a variety of agents for delivery. In some embodiments, an agent is delivered to cells (in vitro delivery). In some embodiments, an agent is delivered to a subject (in vivo delivery). In some embodiments, compositions are provided comprising a surfactant peptide in an aqueous solution.

In some embodiments, the peptide is at a concentration of at least 0.01% (w/v). In some embodiments, the peptide is at a concentration of from about 0.01% (w/v) to about 0.5% (w/v). In some embodiments, the aqueous solution has a pH of from about 6 to about 8. In some embodiments, the aqueous solution has a pH of about 7.5. In some embodiments, the aqueous solution is at an ionic strength of from about 0 M to about 0.3 M. In some embodiments, the aqueous solution is at an ionic strength of about 0.15 M. In some embodiments, the aqueous solution is isotonic.

Payload Agents

In some embodiments, peptides of the invention comprise one or more payload agents, e.g., therapeutic agents or detection agents. Such agents include, e.g., a compound or entity of any chemical class including, for example, polypeptides, nucleic acids, saccharides, lipids, small molecules, metals, or combinations thereof. In some embodiments, an agent is or comprises a natural product in that it is found in and/or is obtained from nature. In some embodiments, an agent is or comprises one or more entities that are man-made in that it is designed, engineered, and/or produced through action of the hand of man and/or is not found in nature. In some embodiments, an agent may be utilized in isolated or pure form; in some embodiments, an agent may be utilized in crude form. Some particular embodiments of agents that may be utilized in accordance with the present invention include small molecules, aptamers, nucleic acids (e.g., siR- NAs, shRNAs, DNA/RNA hybrids, antisense oligonucleotides, ribozymes), peptides, peptide mimetics, and the like.

Detection agents may refer to any element, molecule, functional group, compound, fragment or moiety that is detectable. In some embodiments, a detection entity is provided or utilized alone. In some embodiments, a detection entity is provided and/or utilized in association with (e.g., joined to) another agent. Examples of detection entities include, but are not limited to: various ligands, radionuclides (e.g., $^{3}H$, $^{14}C$, $^{18}F$, $^{19}F$, $^{32}P$, $^{35}S$, $^{135}I$, $^{125}I$, $^{123}I$, $^{64}Cu$, $^{187}Re$, $^{111}In$, $^{90}Y$, $^{99m}Tc$, $^{177}Lu$, $^{89}Zr$ etc.), fluorescent dyes (for specific exemplary fluorescent dyes, see below), chemiluminescent agents (such as, for example, acridinum esters, stabilized dioxetanes, and the like), bioluminescent agents, spectrally resolvable inorganic fluorescent semiconductors nanocrystals (i.e., quantum dots), metal nanoparticles (e.g., gold, silver, copper, platinum, etc.) nanoclusters, paramagnetic metal ions, enzymes (for specific examples of enzymes, see below), colorimetric labels (such as, for example, dyes, colloidal gold, and the like), biotin, dioxigenin, haptens, and proteins for which antisera or monoclonal antibodies are available.

EXEMPLIFICATION

Example 1: Use of Surfactant Peptides to Deliver siRNA to Tumor Cells In Vitro

The present Example describes, among other things, an exemplary use of surfactant peptides for delivery of siRNA to tumor cells in vitro and its cell toxicity and transfection efficacy.

siRNA (Luciferase GL3 duplex) was complexed with Ac-A4K-NH$_2$ (SEQ ID NO: 55), Ac-A3KA3-NH$_2$ (SEQ ID NO:55), Ac-A6K-NH$_2$ (SEQ ID NO: 105), and a control agent (DharmaFECT 1; commercially available lipid transfection agent). The siRNA and peptide complexes arranged into nanospherical structures. A composition comprising the nanospherical structures was provided to tumor cells (MCF-7 cell; breast cancer cell line) in vitro to preliminary transfection efficacy and cell toxicity.

Two methods were utilized for the present Example. For Method 1, MCF-7 cells were cultured on a plate. The siRNA and peptide complexes were added into the culture medium over the cells. The culture dish (96 wells) containing the siRNA and peptide complexes and the cells was incubated for 48 hours. For Method 2, a concentrated suspension of MCF-7 cells ($5 \times 10^6$ cells/ml) was prepared in a tube. The siRNA and peptide complexes were applied into the suspension. The cell mixture was incubated for 1 hour in the tube. The cell mixture was plated in the culture dish and incubated for 48 hours. Luciferase emission from each sample was observed.

Table 4 summarizes experimental conditions e.g., concentration of siRNA and peptide surfactants, charge ratio, and types of siRNA (e.g., Luciferase GL3 duplex or negative control thereof). The buffer used in this Example was Opti-MEM1 (serum-free). As control samples, buffer only, negative control (NC) siRNA with or without the peptide surfactants, DharmaFECT 1 with or without siRNA (or NC siRNA) were tested with the cells.

TABLE 4

| Experimental conditions | | | | |
|---|---|---|---|---|
| Experimental conditions | siRNA [nM] | Surfactant [μM] | Charge ratio (A6K/siRNA) | Remarks |
| A | 25 | 1.15 | 1.0 | — |
| B | 25 | 3.45 | 3.0 | — |
| C | 25 | 5.175 | 4.5 | — |
| D | 25 | 6.9 | 6.0 | — |
| E | 25 | 10.35 | 9.0 | — |
| F | 25 | 15.525 | 13.5 | — |
| G | 250 | 51.75 | 4.5 | — |
| H | 25 | 5.175 | 4.5 | siRNA is NC |
| I | 0 | 5.175 | — | Surfactant peptide only |

Figure 11A:
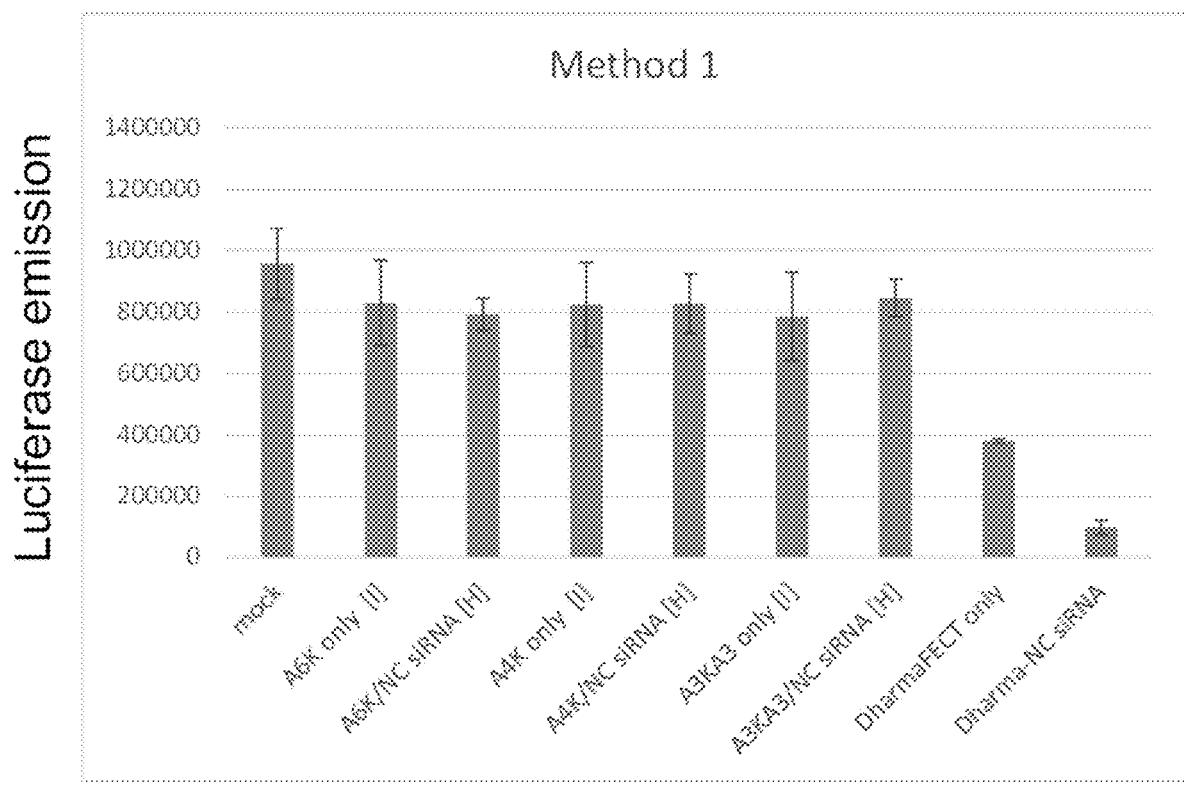
FIGS. 11A and 11B show the cell toxicity data as described in Example 1. The luciferase emission data from the peptides only or the peptides/negative control siRNA are presented. [I] or [H] indicates the experimental condition specified in Table 4.
Figure 11B:
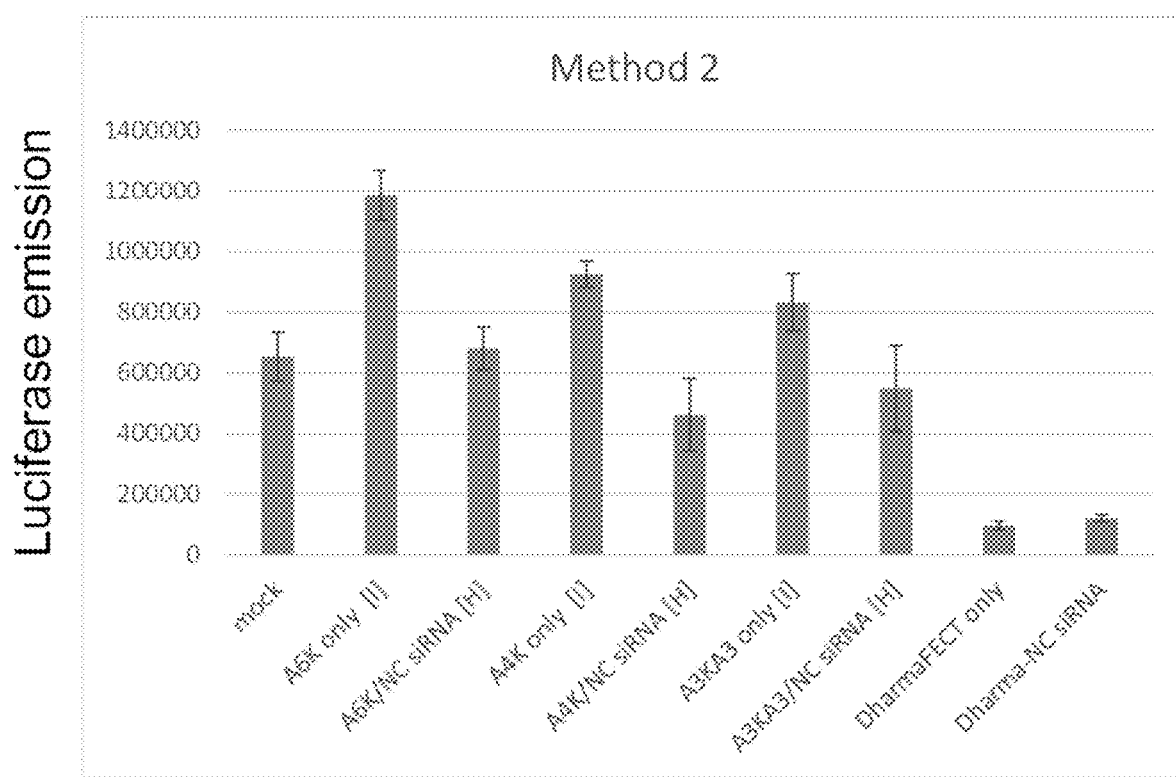

Cell toxicity. For this test, the samples included NC siRNA or did not include siRNA at all. As shown in FIGS. 11A and 11B, the peptides (Ac-A6K-NH$_2$ (SEQ ID NO: 105), Ac-A4K-NH$_2$ (SEQ ID NO: 55) and Ac-A3KA3-NH$_2$ (SEQ ID NO:55)) exhibited a smaller decrease in luciferase emission than DharmaFECT, implying that the peptides are less toxic than DharmaFECT.

Figure 12A:
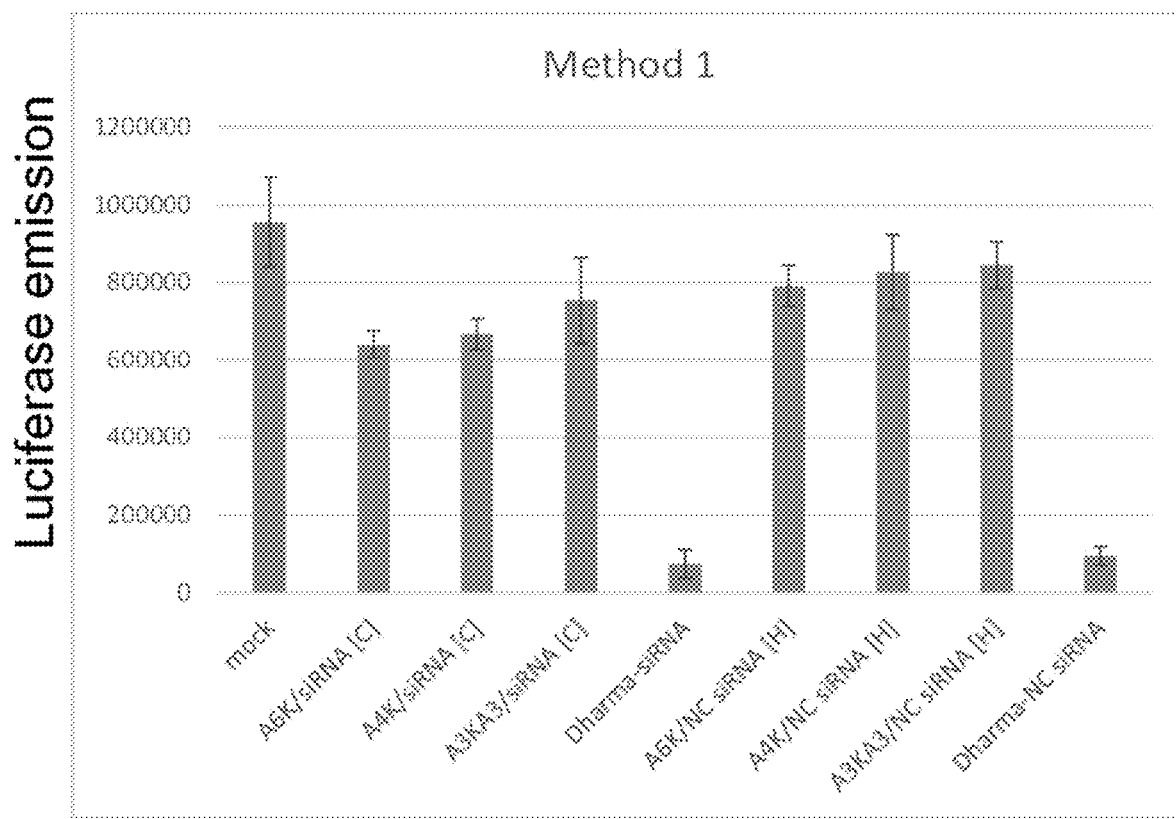
FIGS. 12A-12E depict the transfection efficacy data as described in Example 1.
Figure 12B:
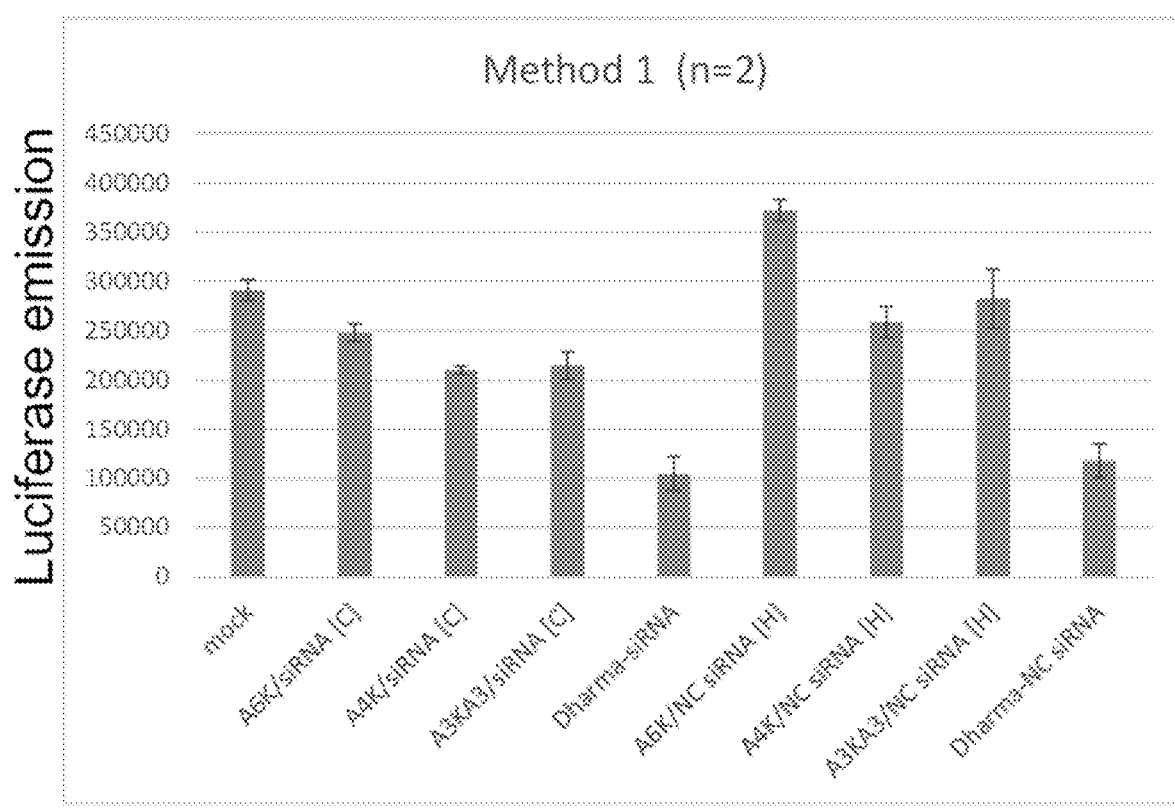
Figure 12C:
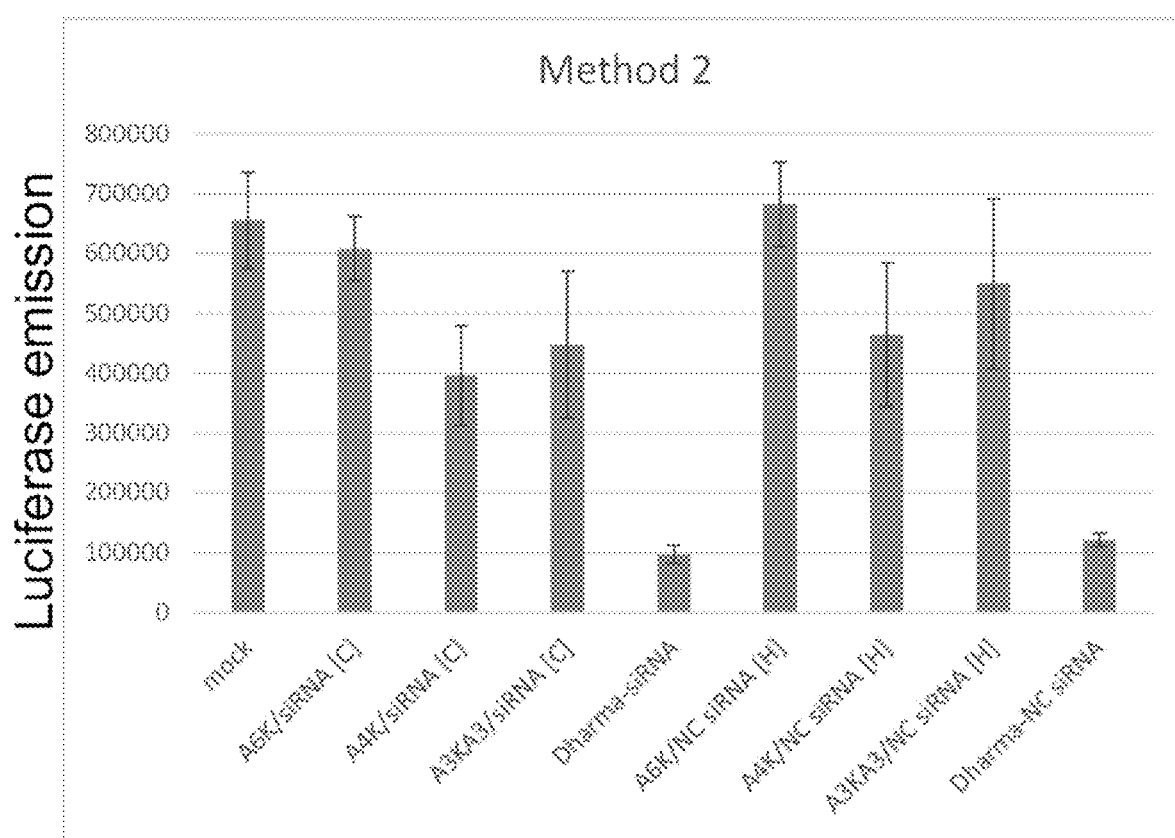
Figure 12D:
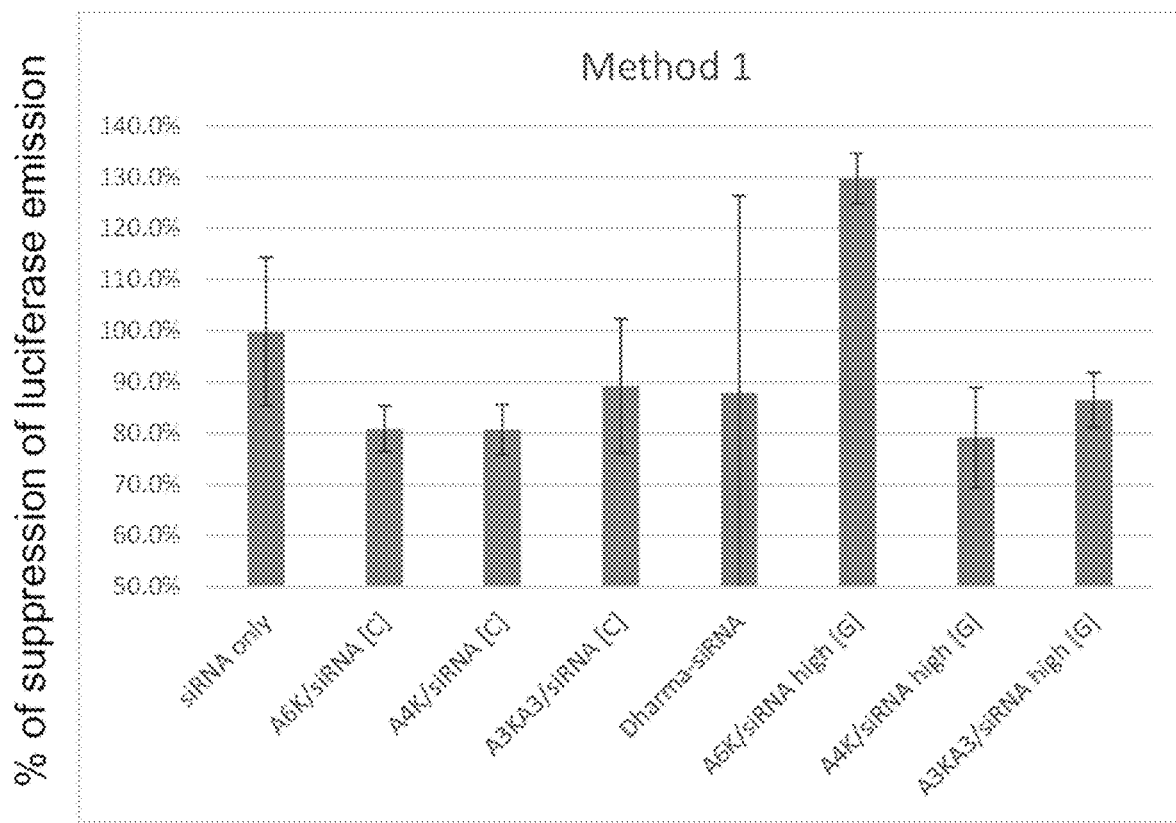
Figure 12E:
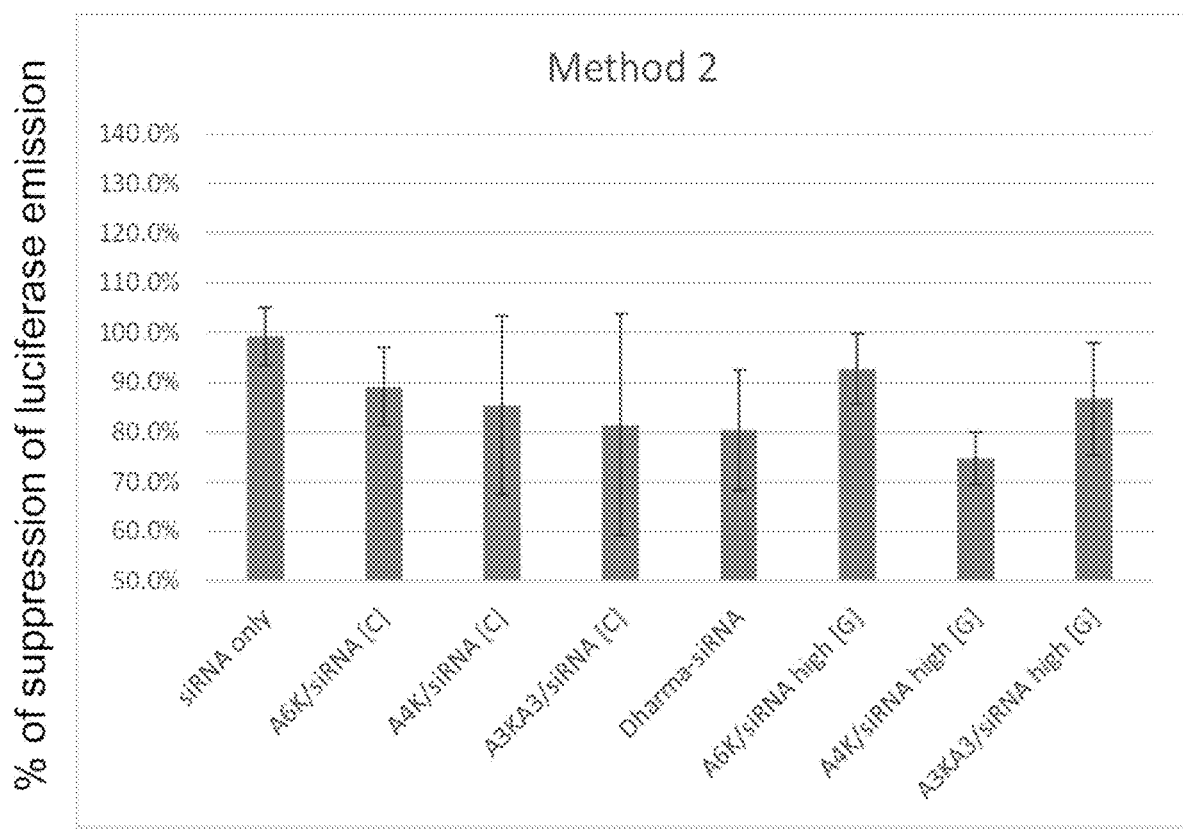

Efficacy. As shown in FIGS. 12D and 12E, luciferase emission was decreased for all surfactants at the charge ratio of 4.5, compared to siRNA only sample. The reduction of luciferase emission from the siRNA and peptide complexes was similar to the one from DharmaFECT (e.g., about 20%). An increase in luciferase emission was observed for A6K/siRNA at high concentration mixture (siRNA 250 nM, A6K 51.75 μM). The high reduction of luciferase emission from DharmaFECT may be originated from the cell toxicity.

Thus, the data in the present Example demonstrates that the peptides or the siRNA and peptide complexes are less toxic than the known transfection reagent, and the siRNA and peptide complexes delivered and effectively suppressed the target gene.

Example 2: Use of Surfactant Peptides to Deliver siRNA to Tumor Cells In Vivo

The present Example describes, among other things, an exemplary use of surfactant peptides for delivery of siRNA to tumor cells in vivo. siRNA is complexed with Ac-A4K-NH$_2$ (SEQ ID NO: 55), Ac-A3KA3-NH$_2$ (SEQ ID NO:55), Ac-A6K-NH$_2$ (SEQ ID NO: 105), or a control peptide. The siRNA and peptide complexes arrange into nanospherical structures. A composition comprising the nanospherical structures is administered to a mouse tumor model. One or more cancer associated genes is suppressed and the size of the tumor decreases.

Example 3: Characterization of Surfactant Peptide/siRNA Complex

The present Example describes, among other things, an exemplary characterization of surfactant peptide/siRNA complex.

Figure 13:
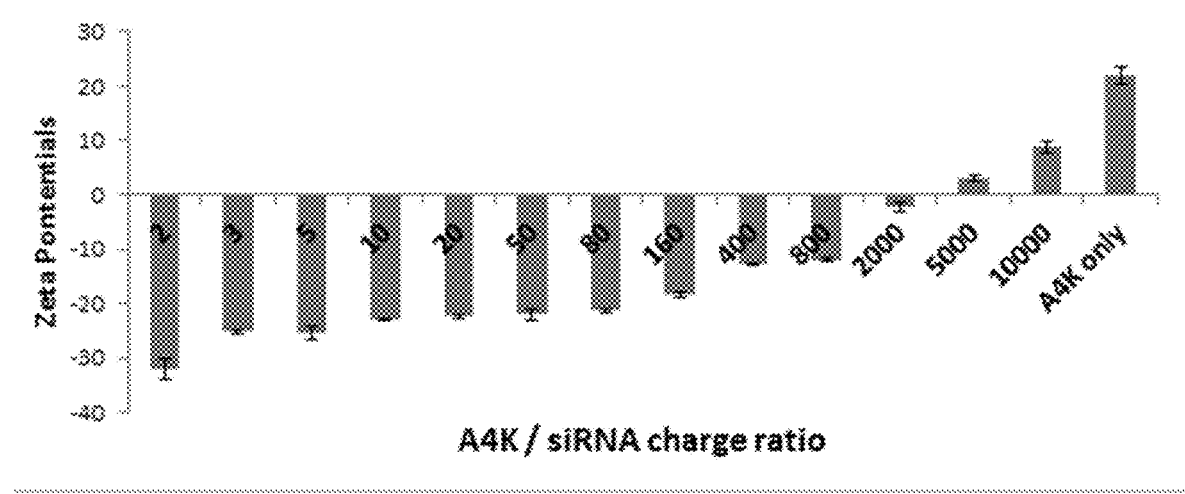
FIG. 13 shows zeta potentials of Ac-A4K-NH$_2$ (SEQ ID NO: 55)/siRIN complex at various charge ratios. The sample size was 3, and the error bars represent standard deviation (SD).

Zeta potentials were measured by Zetasizer Nano ZS (Malvern) to characterize electrokinetic potential of the complex. Ac-A4K-NH$_2$ (SEQ ID NO:55) concentration was 0.5 w/v % in an aqueous solution. siRNA (ribophorin II, RPN2) concentration was controlled for their various charge ratios of A4K/siRNA. The zeta potential of Ac-A4K-NH$_2$ (SEQ ID NO:55) alone was +21.9, which represents that the surface of A4K nanosphere was positively charged because of the primary amine of lysine in Ac-A4K-NH$_2$ (SEQ ID NO:55). The zeta potentials of A4K/siRNA mixtures became more negative with more siRNA as shown in FIG. 13. As the equipment only detects dispersed phases larger than about 3.8 nm and the size of siRNA in water is about 2 nm in diameter, the measurement only reads the electrokinetic potential of Ac-A4K-NH$_2$ (SEQ ID NO:55) or Ac-A4K-NH$_2$ (SEQ ID NO:55)/siRNA complexes, not unassociated siRNA. As such, the result indicates that the negatively charged siRNA molecules were bounded on the positively charged surface of A4K nanospheres. Thus, the data shows that siRNA was successfully complexed with Ac-A4K-NH$_2$ (SEQ ID NO:55).

What is claimed is:

1. A composition comprising a peptide having a nanospheric structure, wherein the peptide comprises the amino acid sequence of AAAAK (SEQ ID NO: 5) or AAAKAAA (SEQ ID NO: 15) wherein the peptide is present at a concentration of at least 0.01% (w/v) in an aqueous solution that has a pH from 6 to 8.

2. The composition of claim 1, wherein the aqueous solution is at an ionic strength of up to 0.3 M.

3. The composition of claim 1, wherein the aqueous solution is isotonic.

4. The composition of claim 1, for use in drug delivery.

5. The composition of claim 4, further comprising an agent for delivery to a subject.

6. The composition of claim 5, wherein the agent is a therapeutic, a drug, or an siRNA.

7. The composition of claim 6, wherein the siRNA is for delivery to a cancer cell.

8. The composition of claim 1, wherein each amino acid is a D-amino acid.

9. The composition of claim 1, wherein any of the peptides is amidated at the C-terminus and acetylated at the N-terminus.

10. The composition of claim 9, wherein the peptide comprises the amino acid sequence of AAAAK (SEQ ID NO: 5).

11. The composition of claim 9, wherein the peptide comprises the amino acid sequence of AAAKAAA (SEQ ID NO: 15).

12. A method of formulating an agent for delivery to a subject, the method comprising a step of contacting the agent with a composition according to claim 5.

13. A method of delivering an agent to a subject, the method comprising administering to the subject a composition according to claim 1.

* * * * *

```
                           SEQUENCE LISTING

<160> NUMBER OF SEQ ID NOS: 105

<210> SEQ ID NO 1
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Ala Ala Ala Lys
1

<210> SEQ ID NO 2
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Lys Ala Ala Ala
1

<210> SEQ ID NO 3
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Val Val Val Lys
1

<210> SEQ ID NO 4
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Lys Val Val Val
1

<210> SEQ ID NO 5
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 5

Ala Ala Ala Ala Lys
1               5

<210> SEQ ID NO 6
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Lys Ala Ala Ala Ala
1               5

<210> SEQ ID NO 7
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Val Val Val Val Lys
1               5

<210> SEQ ID NO 8
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Lys Val Val Val Val
1               5

<210> SEQ ID NO 9
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Ala Ala Ala Lys Ala
1               5

<210> SEQ ID NO 10
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 10

Ala Lys Ala Ala Ala
1               5

<210> SEQ ID NO 11
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Ala Ala Ala Lys Ala Ala
1               5

<210> SEQ ID NO 12
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Ala Ala Lys Ala Ala Ala
1               5

<210> SEQ ID NO 13
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Ala Ala Ala Ala Lys Ala
1               5

<210> SEQ ID NO 14
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Ala Lys Ala Ala Ala Ala
1               5

<210> SEQ ID NO 15
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 15

Ala Ala Ala Lys Ala Ala Ala
1               5

<210> SEQ ID NO 16
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Val Val Val Lys Val Val Val
1               5

<210> SEQ ID NO 17
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Ala Ala Ala Ala Lys Ala Ala
1               5

<210> SEQ ID NO 18
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Ala Ala Ala Lys Lys Ala Ala Ala
1               5

<210> SEQ ID NO 19
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Val Val Val Lys Lys Val Val Val
1               5

<210> SEQ ID NO 20
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 20

Ala Ala Ala Ala Lys Ala Ala Ala
1               5

<210> SEQ ID NO 21
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Val Val Val Val Lys Val Val Val
1               5

<210> SEQ ID NO 22
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Ala Ala Ala Ala Lys Ala Ala Ala Ala
1               5

<210> SEQ ID NO 23
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Val Val Val Val Lys Val Val Val Val
1               5

<210> SEQ ID NO 24
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Ala Ala Ala Ala Lys Lys Ala Ala Ala Ala
1               5                   10

<210> SEQ ID NO 25
<211> LENGTH: 10
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 25

Val Val Val Val Lys Lys Val Val Val Val
1               5                   10

<210> SEQ ID NO 26
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Ala Ala Ala Asp
1

<210> SEQ ID NO 27
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Lys Ala Ala Asp
1

<210> SEQ ID NO 28
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Val Val Val Asp
1

<210> SEQ ID NO 29
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Asp Val Val Val
1

<210> SEQ ID NO 30
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 30

Ala Ala Ala Ala Asp
1               5

<210> SEQ ID NO 31
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Lys Ala Ala Ala Asp
1               5

<210> SEQ ID NO 32
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Val Val Val Val Asp
1               5

<210> SEQ ID NO 33
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Asp Val Val Val Val
1               5

<210> SEQ ID NO 34
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Ala Ala Ala Asp Ala
1               5

<210> SEQ ID NO 35
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 35

Ala Asp Ala Ala Ala
1               5

<210> SEQ ID NO 36
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Ala Ala Ala Asp Ala Ala
1               5

<210> SEQ ID NO 37
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Ala Ala Asp Ala Ala Ala
1               5

<210> SEQ ID NO 38
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Ala Ala Ala Ala Asp Ala
1               5

<210> SEQ ID NO 39
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Ala Asp Ala Ala Ala Ala
1               5

<210> SEQ ID NO 40
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 40

Ala Ala Ala Asp Ala Ala Ala
1               5

<210> SEQ ID NO 41
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Val Val Val Asp Val Val Val
1               5

<210> SEQ ID NO 42
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Ala Ala Ala Ala Asp Ala Ala
1               5

<210> SEQ ID NO 43
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Ala Ala Ala Asp Asp Ala Ala Ala
1               5

<210> SEQ ID NO 44
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Val Val Val Asp Asp Val Val Val
1               5

<210> SEQ ID NO 45
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 45

Ala Ala Ala Ala Asp Ala Ala Ala
1               5

<210> SEQ ID NO 46
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Val Val Val Val Asp Val Val Val
1               5

<210> SEQ ID NO 47
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Ala Ala Ala Ala Asp Ala Ala Ala Ala
1               5

<210> SEQ ID NO 48
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Val Val Val Val Asp Val Val Val Val
1               5

<210> SEQ ID NO 49
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Ala Ala Ala Ala Asp Asp Ala Ala Ala Ala
1               5                   10

<210> SEQ ID NO 50
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 50

Val Val Val Val Lys Lys Val Val Val Val
1               5                   10

<210> SEQ ID NO 51
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 51

Ala Ala Ala Lys
1

<210> SEQ ID NO 52
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 52

Lys Ala Ala Ala
1

<210> SEQ ID NO 53
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 53

Val Val Val Lys
1

<210> SEQ ID NO 54
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
```

```
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 54

Lys Val Val Val
1

<210> SEQ ID NO 55
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 55

Ala Ala Ala Ala Lys
1               5

<210> SEQ ID NO 56
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 56

Lys Ala Ala Ala Ala
1               5

<210> SEQ ID NO 57
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 57

Val Val Val Val Lys
1               5

<210> SEQ ID NO 58
<211> LENGTH: 5
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 58

Lys Val Val Val Val
1               5

<210> SEQ ID NO 59
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 59

Ala Ala Ala Lys Ala
1               5

<210> SEQ ID NO 60
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 60

Ala Lys Ala Ala Ala
1               5

<210> SEQ ID NO 61
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 61

Ala Ala Ala Lys Ala Ala
1               5
```

```
<210> SEQ ID NO 62
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 62

Ala Ala Lys Ala Ala Ala
1               5

<210> SEQ ID NO 63
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 63

Ala Ala Ala Ala Lys Ala
1               5

<210> SEQ ID NO 64
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 64

Ala Lys Ala Ala Ala Ala
1               5

<210> SEQ ID NO 65
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"
```

```
<400> SEQUENCE: 65

Ala Ala Ala Lys Ala Ala Ala
1               5

<210> SEQ ID NO 66
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 66

Val Val Val Lys Val Val Val
1               5

<210> SEQ ID NO 67
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 67

Ala Ala Ala Ala Lys Ala Ala
1               5

<210> SEQ ID NO 68
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 68

Ala Ala Ala Lys Lys Ala Ala Ala
1               5

<210> SEQ ID NO 69
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
```

```
<223> OTHER INFORMATION: /note="N-term Ac"
<220> FEATURE:
<221> NAME/KEY: source
<223> OTHER INFORMATION: /note="C-term NH2"

<400> SEQUENCE: 69

Val Val Val Lys Lys Val Val Val
1               5

<210> SEQ ID NO 70
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 70

Ala Ala Ala Ala Lys Ala Ala Ala
1               5

<210> SEQ ID NO 71
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 71

Val Val Val Val Lys Val Val Val
1               5

<210> SEQ ID NO 72
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 72

Ala Ala Ala Ala Lys Ala Ala Ala Ala
1               5

<210> SEQ ID NO 73
<211> LENGTH: 9
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 73

Val Val Val Val Lys Val Val Val Val
1               5

<210> SEQ ID NO 74
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 74

Ala Ala Ala Ala Lys Lys Ala Ala Ala Ala
1               5                   10

<210> SEQ ID NO 75
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 75

Val Val Val Val Lys Lys Val Val Val Val
1               5                   10

<210> SEQ ID NO 76
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 76

Ala Ala Ala Asp
1
```

```
<210> SEQ ID NO 77
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 77

Lys Ala Ala Asp
1

<210> SEQ ID NO 78
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 78

Val Val Val Asp
1

<210> SEQ ID NO 79
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 79

Asp Val Val Val
1

<210> SEQ ID NO 80
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"
```

```
<400> SEQUENCE: 80

Ala Ala Ala Ala Asp
1               5

<210> SEQ ID NO 81
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 81

Lys Ala Ala Ala Asp
1               5

<210> SEQ ID NO 82
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 82

Val Val Val Val Asp
1               5

<210> SEQ ID NO 83
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 83

Asp Val Val Val Val
1               5

<210> SEQ ID NO 84
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
```

```
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 84

Ala Ala Ala Asp Ala
1               5

<210> SEQ ID NO 85
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 85

Ala Asp Ala Ala Ala
1               5

<210> SEQ ID NO 86
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 86

Ala Ala Ala Asp Ala Ala
1               5

<210> SEQ ID NO 87
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 87

Ala Ala Asp Ala Ala Ala
1               5

<210> SEQ ID NO 88
<211> LENGTH: 6
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 88

Ala Ala Ala Ala Asp Ala
1               5

<210> SEQ ID NO 89
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 89

Ala Asp Ala Ala Ala Ala
1               5

<210> SEQ ID NO 90
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 90

Ala Ala Ala Asp Ala Ala Ala
1               5

<210> SEQ ID NO 91
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 91

Val Val Val Asp Val Val Val
1               5
```

```
<210> SEQ ID NO 92
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 92

Ala Ala Ala Asp Ala Ala
1               5

<210> SEQ ID NO 93
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 93

Ala Ala Ala Asp Asp Ala Ala Ala
1               5

<210> SEQ ID NO 94
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 94

Val Val Val Asp Asp Val Val Val
1               5

<210> SEQ ID NO 95
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"
```

```
<400> SEQUENCE: 95

Ala Ala Ala Ala Asp Ala Ala Ala
1               5

<210> SEQ ID NO 96
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 96

Val Val Val Val Asp Val Val Val
1               5

<210> SEQ ID NO 97
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 97

Ala Ala Ala Ala Asp Ala Ala Ala Ala
1               5

<210> SEQ ID NO 98
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 98

Val Val Val Val Asp Val Val Val Val
1               5

<210> SEQ ID NO 99
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
```

```
<223> OTHER INFORMATION: /note="N-term Ac"
<220> FEATURE:
<221> NAME/KEY: source
<223> OTHER INFORMATION: /note="C-term NH2"

<400> SEQUENCE: 99

Ala Ala Ala Ala Asp Asp Ala Ala Ala Ala
1               5                   10

<210> SEQ ID NO 100
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 100

Val Val Val Val Lys Lys Val Val Val Val
1               5                   10

<210> SEQ ID NO 101
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Ala Ala Ala Ala Ala Ala Lys
1               5

<210> SEQ ID NO 102
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Ala Ala Ala Ala Ala Ala Ala Ala Ala Lys
1               5                   10

<210> SEQ ID NO 103
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Ala Ala Ala Ala Ala Lys
1               5

<210> SEQ ID NO 104
<211> LENGTH: 14
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Ala Ala Ala Ala Ala Ala Lys Lys Ala Ala Ala Ala Ala
1               5                   10

<210> SEQ ID NO 105
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term Ac"
<220> FEATURE:
<221> NAME/KEY: source
<223> OTHER INFORMATION: /note="C-term NH2"

<400> SEQUENCE: 105

Ala Ala Ala Ala Ala Ala Lys
1               5
```